US007566765B2

(12) United States Patent
Kinsella

(10) Patent No.: US 7,566,765 B2
(45) **Date of Patent: *Jul. 28, 2009**

(54) HETEROCYCLIC COMPOUNDS CONTAINING A NINE-MEMBERED CARBON-NITROGEN RING

(75) Inventor: Todd M. Kinsella, Redwood City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 11/033,416

(22) Filed: Jan. 10, 2005

(65) Prior Publication Data

US 2005/0227291 A1 Oct. 13, 2005

Related U.S. Application Data

(63) Continuation-in-part of application No. PCT/US03/27371, filed on Aug. 30, 2003, and a continuation-in-part of application No. 09/800,770, filed on Mar. 6, 2001, now Pat. No. 7,105,341.

(60) Provisional application No. 60/187,130, filed on Mar. 6, 2000, provisional application No. 60/619,420, filed on Oct. 14, 2004.

(51) Int. Cl.
*A61K 38/12* (2006.01)
*A61K 38/06* (2006.01)

(52) U.S. Cl. ....................... 530/317; 530/331; 530/333; 435/4

(58) Field of Classification Search ....................... None
See application file for complete search history.

(56) References Cited

U.S. PATENT DOCUMENTS

| | | | | |
|---|---|---|---|---|
| 4,560,515 | A | 12/1985 | Stoutamire et al. | |
| 5,596,078 | A | 1/1997 | Andersson et al. | |
| 5,656,726 | A * | 8/1997 | Rosenberg et al. | 530/326 |
| 2003/0068649 | A1 | 4/2003 | Doberstein | |
| 2003/0078369 | A1 | 4/2003 | Meinke et al. | |

(Continued)

FOREIGN PATENT DOCUMENTS

DE 1009191 5/1957

(Continued)

OTHER PUBLICATIONS

Kick et al. 1997 Chemistry and Biology 4:297-307.*

(Continued)

*Primary Examiner*—Christopher Low
*Assistant Examiner*—Christopher M. Gross
(74) *Attorney, Agent, or Firm*—James S. Keddie; Carol L. Francis; Travis Young

(57) ABSTRACT

The present invention provides heterocyclic compounds having a nine-membered ring of three repeating C—C—N subunits covalently bound to each other through amide bonds, and variable side groups linked to a central C of each subunit. Also described herein are cells containing the cyclic compounds, methods of screening those cells to identify a cyclic compound of interest, and libraries of cyclic compounds and their encoding nucleic acids. The subject compounds may be employed in a variety of research and medical applications, including methods of treating a patient for hepatitis C infection.

4 Claims, 4 Drawing Sheets

U.S. PATENT DOCUMENTS

| | | |
|---|---|---|
| 2003/0166138 A1 | 9/2003 | Kinsella et al. |
| 2003/0211982 A1 | 11/2003 | Saragovi et al. |
| 2004/0014100 A1 | 1/2004 | Lorenz et al. |
| 2004/0053324 A1 | 3/2004 | Wong |
| 2004/0180353 A1 | 9/2004 | Booher |
| 2004/0236519 A1 | 11/2004 | Marshall et al. |
| 2004/0248220 A1 | 12/2004 | Blaschuk et al. |
| 2005/0203025 A1 | 9/2005 | Blaschuk et al. |
| 2005/0227291 A1 | 10/2005 | Kinsella |

FOREIGN PATENT DOCUMENTS

| | | |
|---|---|---|
| JP | 06172385 A2 | 6/1994 |
| WO | WO 97/10839 A1 | 3/1997 |
| WO | WO 00/18790 A1 | 4/2000 |
| WO | WO 00/36093 A3 | 6/2000 |
| WO | WO0036093 A2 | 6/2000 |
| WO | WO0071702 A1 | 11/2000 |
| WO | WO 01/07042 A1 | 2/2001 |
| WO | 01/57183 | 8/2001 |
| WO | WO0155452 A1 | 8/2001 |
| WO | WO 01/66565 A2 | 9/2001 |
| WO | WO 03/066673 A1 | 8/2003 |
| WO | WO 03/072034 A3 | 9/2003 |
| WO | WO 03/092631 A2 | 11/2003 |
| WO | WO 03/093300 A2 | 11/2003 |
| WO | WO 2004/052915 A2 | 6/2004 |
| WO | WO 2004/052916 A1 | 6/2004 |

OTHER PUBLICATIONS

Parsons. 1976 Peptide Hormones University Park Press pp. 1-6.*
Alsina et al 1999 Chem. Eur. J. 5:2787-2795.*
Russek et al 2000 PNAS 97:8600-8605 plus supplementary GenBank accession No. AAF88061.*
Scott et al. 2001 Chemistry & Biology 8:801-815.*
Kinsella et al (2002 JBC 277:37512-37518).*
Xie et al (1994 Faraday Discuss. 99:233-243).*
Guo et al (1989 J. Electroanal. Chem 266:379-396).*
CAS registry No. 124346-06-1 (database entered Dec. 22, 1989; Downloaded Sep. 29, 2008).*
Brennand, D.M. et al. "Identification of a cyclic peptide inhibitor of platelet-derived growth factor-BB receptor-binding and mitogen-induced DNA synthesis in human fibroblasts." *FEBS Lett.* Aug. 11, 1997;413(1):70-4.
Camarero et al., "Chemical Synthesis of a Circular Protein Domain: Evidence for Folding-Assis," *Angew. Chem.* 37(3):347-349 (1998).
Camarero and Muir, "Biosynthesis of a Head-to-Tail Cyclized Protein with Improved Biological Activity," *J Am Chem Soc*; 1999; 121(23); 5597-5598.
Camarero and Muir, "Chemoselective backbone cyclization of unprotected peptides," *Chem Commun* 1997(15):1369-1370 (1997).
Eriksson, J.E. et al. "Rapid microfilament reorganization induced in isolated rat hepatocytes by microcystin-LR, a cyclic peptide toxin." *Exp Cell Res.* Nov. 1989:185(1):86-100.
Evans, T.C. Jr, et al. "Semisynthesis of cytotoxic proteins using a modified protein splicing element." *Protein Sci.* Nov. 1998;7(11)2256-64.
Evans, T.C. Jr, et al., "The cyclization and polymerization of bacterially expressed proteins using modified self-splicing inteins." *J Biol Chem.* Jun. 25, 1999;274(26):18359-63.
Friedler, A., et al. "Backbone cyclic peptide, which mimics the nuclear localization signal of human immunodeficiency virus type 1 matrix protein, inhibits nuclear import and virus production in nondividing cells." *Biochemistry.* Apr. 21, 1998;37(16):5616-22.
Goldenberg, D.P. and Creighton, T.E. "Circular and circularly permuted forms of bovine pancreatic trypsin inhibitor." *J Mol Biol.* Apr. 5, 1983;165(2):407-13.
Hruby, V.J., et al., "Emerging approaches in the molecular design of receptor-selective peptide ligands: conformational, topographical and dynamic considerations." *Biochem J.* Jun. 1, 1990;268(2):249-62.

Hruby, V.J. "Conformational restrictions of biologically active peptides via amino acid side chain groups." *Life Sci.* Jul. 19, 1982;31(3):189-99.
Iwai, H. and Pluckthun, A. "Circular beta-lactamase: stability enhancement by cyclizing the backbone." *FEBS Lett.* Oct. 8, 1999;459(2):166-72.
Jackson, D.Y. et al., "Enzymatic Cyclization of Linear Peptide Esters Using Subtiligase," *J Am Chem Soc* 117(2):819-820 (1995).
Jois, S.D. et al., "A Ca2+ binding cyclic peptide derived from the alpha-subunit of LFA-1: inhibitor of ICAM-1/LFA-1-mediated T-cell adhesion." *J Pept Res.* Jan. 1999;53(1):18-29.
Kimura, K., et al. "Propeptin, a new inhibitor of prolyl endopeptidase produced by Microbispora. I. Fermentation, isolation and biological properties." *J Antibiot* (Tokyo). May 1997;50(5):373-8.
Koivunen, E., et al., "Phage libraries displaying cyclic peptides with different ring sizes: ligand specificities of the RGD-directed integrins." *Biotechnology* (NY). Mar. 1995;13(3):265-70.
Scott, C.P. et al. "Production of cyclic peptides and proteins in vivo." *Proc Natl Acad Sci USA.* Nov. 23, 1999;96(24):13638-43.
Southworth, M.W. et al., "Control of protein splicing by intein fragment reassembly." *EMBO J.* Feb. 16, 1998;17(4):918-26.
Tam, J.P. and Lu, Y.A. "A biomimetic strategy in the synthesis and fragmentation of cyclic protein." *Protein Sci.* Jul. 1998;7(7):1583-92.
Wood, D.W., et al. "A genetic system yields self-cleaving inteins for bioseparations." *Nat Biotechnol.* Sep. 1999;17(9):889-92.
Zhang, L. and Tam, J.P., "Synthesis and Application of Unprotected Cyclic Peptides as Building Blocks," *J Am Chem Soc* 119(10):2363-2370 (1997).
Evans, T.C. et al., "Protein *trans*-Splicing and Cyclization by a Naturally Split Intein from the *dnaE* Gene of *Synechocystis* Species PCC6803," *J Biol Chem* 275(13):9091-9094 (2000).
Evans et al., The In Vitro Ligation of Bacterially Expressed Proteins Using an Intein From Methanobacterium Thermoautotorophicum, J. of Biol. Chem., 1999, 274(7): 3923-3926.
Wu et al., Protein Trans-Splicing and Functional Mini-Inteins of a Cyanobacterial DNAB Intein, Biochimica et Biophysica Acta, 1998, 1387.
Lew et al., Protein Splicing In Vitro With a Semisynthetic Two-Component Minimal Intein, J. of Biol. Chem., 1998, 273(26), 15887-015890.
Lew et al., Characteristics of Protein Splicing in Trans Mediated by a Semisynthetic Split Intein, Biopolymers, 1999, 51(5): 355-62.
Wu et al., Protein Trans-Splicing by a Split Intein Encoded in a Split DNAE Gene of *Synechocystis* sp. PCC6803, Proc. Natl. Acad. Sci., 1998, 95: 9226-9231.
Southworth et al., Control of Protein Splicing by Intein Fragment Reassembly, EMBO Journal, 1998, 17(4): 918-926.
Germino, F., et al. Screening for in vivo protein-protein interactions. Proc Natl Acad Sci USA. 1993, vol. 90, pp. 933-937.
Paolini et al. Ubiquitination and degradation of Syk and ZAP-70 protein tyrosine kinases in human NK cells upon CD16 engagement. PNAS. 2001, vol. 98, No. 17, pp. 9611-9616.
Shimura et al. Ubiquitination of a new form of alpha-synuclein by Parkin from human brain: Implications for Parkinson's Disease. Science. 2001, vol. 293, pp. 263-269.
Strayhorn et al. A novel in vitro assay for deubiquitination of I(kappa)B(alpha). Archives of Biochemistry and Biophysics. 2002, vol. 400, No. 1, pp. 76-84.
Rudinger, "Characteristics of the amino acids as components of a peptide hormone sequence", Institut fur Molekularbiologie und Biophysik, 1976, pp. 1-6.
Poteau et al., "All-cis cyclic peptides", J. American Chemical Society (2005), 127(40), pp. 13875-13889.
Yasukawa et al., "Inhibition of experimental choroidal neovascularization in rats by an αvintegrin antagonist", Current Eye Research (2004), 28(5), pp. 359-366.
Lowe et al., "Dipole interaction model predicted ππ* circular dichroism of cyclo(L-Pro)3 using structures created by semi-empirical, ab initio, and molecular mechanics methods", Journal of Peptide Research (2003), 61(4), 189-201.

Bolm et al., "A novel enantiopure praline-derived triazacyclononame: synthesis, structure and application of its manganese complex", Chemical Communications (Cambridge) (2000), (24), pp. 2435-2436.
Malon et al., "Vibrational circular dichroism of cyclo (triL-2-azetidinecarbonyl)", Pep. 192, Proc. Eur. Pept. Symp., 22nd (1993), Meeting Date 1992.
Zwahlen et al., Separation of overlapping multiplets in a two-dimensional NMR spectrum by injection of magnetization. Angewandte Chemie (1992), 104(9), pp. 1248-1251.
Ramakrishnan et al., "Stereochemical studies of cyclic peptides. XIV. Conformational analysis of cyclic tripeptides", International Journal of Peptide & Protein Research (1987), 29(6), pp. 657-671.
Symersky et al., "Structure of cyclo(triDazetidine-2-carboxylic acid)", Acta Crystallographica, Section C: Crystal Structure Communications, (1988), C44(1), 148-159.
Rothe et al., "Secondary all-L-cyclotripeptides", Pept., Proc. Eur. Pept. Symp., 18th (1984), pp. 573-576.
Rothe et al., "Synthesis of cyclic tripeptides containing CONH groups", Chem. Pept. Proteins, Proc. USSR-FRG Symp., 4th (1984), Meeting Date 1982, p. 121-126.
Faehnle et al., "Syntheses and reactions of peptide cyclols", Chem. Pept. Proteins, Proc. USSR-FRG Symp., 4th (1984), Meeting Date 1982, pp. 115-120.
Shekar et al., "Pyrrolidine ring conformations in prolyl peptides from carbon13 spinlattice relaxation times", International Journal of Peptide & Protein Research (1984), 23(2), pp. 166-173.
Kessler et al., "Peptide conformations. 22. The conformation of cyclo[Pro2(NB)Gly] in crystal and solution by x-ray analysis and one and two-dimensional NMR spectroscopy", Liebigs Annalen der Chemie (1983), (2), pp. 231-247.
De Leeuw et al., "E. Peptide conformations. 20. Conformational analysis of proline rings from proton spin-spin coupling constants and forcefield calculations: application to three cyclic tripeptides", Journal of the American Chemical Society (1983), 105(8), pp. 2237-2246.
Kessler et al., "Peptide conformation. 17. cyclo(LProLProDPro). Conformational analysis by 270 and 500-MHZ one and two-dimensional proton NMR spectroscopy", Journal of the American Chemical Society (1982), 104(23), pp. 6297-6204.
Kessler et al., "Peptide conformations. Part 16. Solidstate carbon13 NMR spectra of cyclotriprolines", Angewandte Chemie (1982), 94(9), p. 703.
Kessler et al., "Peptide conformation. 18. Analysis of the conformational equilibrium of cyclo[Pro-NBGly2] by means of two-dimensional NMR spectroscopy", Journal of the American Chemical Society (1982), 104((16), pp. 4486-4487.
Rothe et al., "Cyclic peptides. Part 30. Macrocyles from D and L-proline residues", Angewandte Chemie (1982), 94(3), pp. 220-221.
Kessler et al., "NMR analysis and conformation of cyclotripolines", Pep. Synth., Struct., Funct., Proc. Am. Pept. Symp., 7th (1981), pp. 335-338.
Rothe et al., "Cyclol formation during tripeptide cyclizations. Synthesis of a secondary cyclotripeptide, cyclo(DPhe-LProLPro)", Pept.: Synth., Struct., Funct., Proc. Am. Pept. Symp., 7th (1981), pp. 89-92.
Bats et al., "Conformation and structure of cyclo(NbenzylglycylLprolyL-prolyl-)", Acta Crystallographica, Section B: Structural Crystallography and Crystal Chemistry (1982), B38(3), pp. 1004-1007.
Kessler et al. "Peptide conformation. 12. Conformation of cyclo(L-Pro3) in solution", Journal of Organic Chemistry (1981), 46(19), pp. 3892-3895.
Kessler, "Peptide confirmations. Part VIII. Conformational mobility of the backbone of cyclic tripeptides", Stereodyn. Mol. Syst., Proc. Symp. (1979), pp. 187-196.
Bats et al., "Peptide conformations. 6. The boat conformation of cyclo[Lro2D-Pro]", Angewandte Chemie (1979), 91(7), 538-539.
Vicar et al. 13C13C couplings in 13Clabeled cyclo(tri-L-prolyl) and the pyrrolidine ring conformation), Biopolymers (1979), 18(4), pp. 1021-1022.
Boni et al., "Cyclic peptides. Part XX. Synthesis and circular dichroism characterization of Lazetidine2-carboxylic acid cyclic peptides", Biopolymers (1978), 17(10), 2385-2599.
Anteunis et al., "Ring conformational aspects of praline and hydroxyproline. High conformational purity of praline in diketopiperazined and hydantoins", Bulletin des Societes Chimiques Belges (1978), 87(1), pp. 41-60.
Meraldi et al., "Cyclic peptides. Part XXI. Solution conformations of some azetidine cyclic peptides", Biopolymers (1978), 17(10), 2401-2413.
Rothe et al., "Interchain reactions (cyclooligomerizations) during the cyclization of resinbound peptides", Pept., Proc. Am. Pept. Symp., 5th (1977),pp. 506-509.
Madison, "Flexibility of the pyrrolidine ring in proline peptides", Biopolymers (1977), 16(12), 2671-2692.
Deslauriers et al., "Conformational flexibilty of cyclo(triprolyl) in solution -a carbon-13 NMR investigation", Pept.: Chem., Struct. Biol., Proc. Am. Pept. Symp., 4th (1975), 91-96.
Druyan et al., A crystallographic study of cyclic(triprolyl): flexibilty of prolyl residues, Pept.:, Chem., Struct. Biol., Proc. Am. Pept. Symp., 4th (1975), 85-89.
Rothe et al., "Studies on the cyclization tendency of peptides", Chem. Biol. Pept., Proc. Am. Pept. Symp., 3rd (1972), pp. 51-57.
Siemion et al., "Effect of the distance of the proline carbonyl from β and γ carbons on the position of the carbon-13 NMR signals", Angewandte Chemie (1975), 87(19), pp. 712-714.
Rothe et al., "Problem of cyclotripeptide synthesis", Pept., Proc. Eur. Pept. Symp., 11th (1973) Meeting Date 1971, pp. 388-399.
Kartha et al., "Crystal structure and molecular conformation of cycloLprolylLprolylL-hydroxyproline, a cyclic tripeptide", Acta Crystallographica, Section B: Structural Crystallography and Crystal Chemistry (1975), B31(8), pp. 2035-2039.
Dale et al., "Conformational processes in simple cyclic peptides", Acta Chemica Scandinavica Series B: Organic Chemistry and Biochemistry (1975) B29(3), pp. 353-361.
Deslauriers et al., "Conformational mobility of the pyrrolidine ring of praline in peptides and peptide hormones as manifest in carbon 13 spinlattice relaxation times", Journal of Biological Chemistry (1974), 249(21), pp. 7006-7010.
Kartha et al., "Structure and conformation of a cyclic tripeptide", Nature (London, United Kingdom) (1974), 247(5438), pp. 204-205.
Torchia et al., "Evidence for stereospecific collision complexes of cyclo(triLprolyl) with benzene", Biopolymers (1972), 11(3), pp. 653-659.
Knof et al., "Binding of benzyl alcohol to the peptide CO group of cyclotriLprolyl studied by infrared spectroscopy", Biopolymers (1972), 11(3), pp. 731-733.
Deber et al., Small cyclic proline peptides: ultraviolet absorpotion and circular dichroism. Peptides: Chem. Biochem., Proc. Amer. Peptide Symp., 1st (1970), Meeting Date 1968, pp. 163-173.
Venkatachalam et al., "Stereochemical studies on cyclic peptides. II. Molecular structure of cyclotriprolyl", Biochimica et Biophysica Acta, Protein Structure (1968), 168(3), pp. 397-401.
Rothe et al., "Cyclic peptides. XI. Synthesis of cyclotri-L-prolyl, a cyclotripeptide with a nine-membered ring", Angew. Chem. (1965), 77(7), p. 346.
Bamford et al., "The structure of macrocyclic glycine peptides", Journal of the American Chemical Society (1955), 77, pp. 6368-6369.
Brockmann et al., "Formation of cyclic polypeptides", Naturwissenschaften (1954), 41, pp. 37-38.
Winitz et al., "A method for the synthesis of cyclic polypeptides", Journal of the American Chemical Society (1953), 75, p. 3041.
Kunihiro et al., "A novel antifuntal cyclic tetrapeptide produced by *Streptomyces lavendulae* H6398 Sy2:", Journal of Antibiotics (2003), 56(1), pp. 30-33.
Colletti et al., "Broad spectrum antiprotozoal agents that inhibit histone deacetylase: structure-activity relationships of apicidin. Part 2", Bioorganic & Medicinal Chemistry Letters (2001), 11(2), p. 113-117.
Colletti et al., "Tryptophan-replacement and indole-modified apicidins: synthesis of potent and selective antiprotozoal agents", Tetrahedron Letters (2000), 41(41), pp. 7825-7829.

Kahn et al., "The design and synthesis of mimetics of peptide β-turns", Journal of Molecular Recognition (1988), 1(2), pp. 75-79.
Rasmussen et al. "Isolation and biological activities of four toxins from *Helminthosporium carbonum*", Plant Physiology (1988), 86(1), p. 187-191.
Tanis et al., "A new host specific toxin from *Helminthosporium carbonum*", Heterocycles (1986), 24(12), pp. 3423-3431.
Chipens et al. "Elongated and cyclic analogs of tufsin and rigin", Pept., Proc. Eur. Pept. Symp., $16^{th}$ (1981) Meeting Date 1980, 445-450.
Scott et al., "Structural requirements for the biosynthesis of backbone cyclic peptide libraries," Chemistry Biology 8 (2001) pp. 801-815.
Alsina et al., "Solid-Phase Synthesis with Tris(alkoxy)benzyl Backbone Amide Linkage (BAL)," Chem. Eur. J. (1999), 5, No. 10, pp. 2787-2795.
Kick et al., Structure-based design and combinatorial chemistry yield low nanomolar I nhibitors of cathepsin D, Chemistry & Biology, (1997), (4) pp. 297-307.
Lambert et al., "The synthesis of cyclic peptides", J. Chem. Socl., Perkins Trans 1, 2001, pp. 471-484.
Day et al., "Creatinine, Lactam and Cyclic Peptide Formation by Action of $C_2N_2$ on Creatine, w-Amino Acids and Peptides", Peptide Research, vol. 3, No. 4 (1990), pp. 169-175.
Kessler et al., "The Confirmation of cyclo [$Pro_2$-(NB)Gly] in Crystal and Solution by X-ray Analysis and One- and Two-dimensional NMR Spectroscopy", Liebigs Ann. Chem. (1983), pp. 231-247.
Kinsella et al., "Retrovirally Delivered Random Cyclic Peptide Libraries Yield Inhibitors of Interleukin-4 Signaling in Human B Cells", J. Biological Chemistry, vol. 277, No. 40, Oct. 2002, pp. 37512-37518.
Kessler et al., "Synthesis and Conformation in the Crystal and in Solution", Chem. Ber. 116, pp. 3164-3181 (1983).
Dale, "Conformational Aspects of Many Membered Rings", Angew. Chem. Internat. Edit., vol. 5 (1966), No. 12, pp. 1000-1021.
Rothe et al., "Macrocycles of D- and L-Proline Residues", Agnew. Chem. Int. Ed. Engl. 21 (1982), No. 3, pp. 220-221.
Asher et al., "Cyclo $(L\text{-prolylglycyl})_3$ and Its Sodium, Potassium, and Calcium Ion Complexes: A Raman Spectroscopic Study", Biochemistry, (1980), vol. 19, pp. 1805-1813.
Vicar et al., "Synthesis and Spectral Properties of Cyclotripeptides Containg 2-AzetidineCarboxylic Acid or Proline", Collection Czechoslov. Chem. Commun., vol. 42, (1977), pp. 2701-2716.
Rothe, Beckmann- und Schmidt-Umlagerung alicyclischer Diketone. Synthese von Cyclo-diamiden des mitterleren Ringbereichs[3]), Angew, Chem, 69, 341 (1957), pp. 783-795.
Rydon et al., "The Condensation-polymerisation of Some Polyglycine Esters and Azides", Imperial College of Science and Technologgy, South Kensington, London, S.W.7. College of Technology, University of Manchester, Manchester, 1, (Mar. 11, 1955), pp. 2542-2549.
Siemion et al., "Influence of the Distance of the Proline Carbonyl from the β and γ Carbon on the $^{13}C$ Chemical Shifts", Angew. Chem. 87, 702 (1975).
Rydon et al., "The Self-condensation of the Esters of Some Peptides of Glycine and Proline", J. Polymer Sci., (1954), 12, 253, pp. 3642-3650.
Iseli et al., "13. MO-Calculation of the Optical Activity of Oligopeptides. II. Open-Chain Conformations. Comparison with Some Cyclic Systems", Helvetica Chimica Acta, vol. 61, Fasc. 1 (1978), Nr. 13, pp. 171-183.
Titlestad, "Cyclic Peptides of Sarcosine Synthesis and Conformation", Acta Chem. Scand. B29 (1975), No. 2, pp. 153-167.
Schaug, "Ring Inversion in Cyclotrisarcosyl", Acta Chem. Scand. 25 (1971) No. 7, pp. 2771-2772.
Kessler et al., "Conformational Equilibrium in Backbone of Cyclic Tripeptides", J. American Chem. Soc. (1978), 100:8, pp. 2548-2550.
Kessler et al., "Peptide Conformation, IX Conformational Studies on Cyclotripeptides Containjng N-Benzyl-Glycine", Israel J. Chem, vol. 20, (1980) pp. 188-195.
Hioki et al., "Synthesis of N-substituted cyclic triglycines and their response to metal ions", Tetrahedron Letters, 45 (2004), pp. 1091-1094.
Ruckle et al., "Pseudo-Prolines in Cyclic Peptides: Conformational Stabilisation of cyclo[Pro-Thr ($\Psi^{Me,Me}$pro)-Pro]", Tetahedron 55 (1999), pp. 11281-11288.
Smith, "cyclo (Glycylglycl -DL-prolyl)", Analyst (1953), 78, 722, pp. 3985-3987.
Sonntag et al., "Functionalized Cyclotripoline—A Bowl-Shaped Tripodal Scaffold", Synlett (2004), No. 7, pp. 1270-1272.
Groth, "Crystal Conformation of Cyclodeasarcosyl, $4CH_3OH$ at —160° C.", Acta Chem. Scand. A30 (1976), No. 10, pp. 840-842.
Groth, "Crystal Conformation of Cyclotrisarcosyl at—160° C.", Acta Chem. Scand. A30 (1976), No. 10, pp. 838-839
Dale et al., Cyclic Oligopeptides of Sarconsine (N-Methylglycine), Chemical Communications (1969), pp. 656-659.
Sheehan et al., "A New Method for the Synthesis of Macrocyclic Peptides", Dept. Chem, Massachusetts Institute of Technology (1954), vol. 76, pp. 6329-6330.
Schwyzer et al., "Verdoppelungsreaktionen beim Ringschluss von Peptiden. 1. Synthese von Gramicidin S und von bis-homo-Gramicidin S aus den Pentapeptid-Einheiten", Helvetica Chimica Acta, 35, 229 (1952), pp. 2186-2189.
Boissonnas et al., "Sur la cyclisation des polypeptides", vol. XXXV, Fasciculus VII (1952), No. 277, pp. 2229-2235.
Magee et al., "The Application of the Curtius Reaction to the Polymerization of Triglycine", Dept. Chem, University of Pittsburgh, Pittsburgh, PA., (1949), vol. 781, pp. 1515-1516.
Nam et al., "Conformationally Constrained Peptide Analogues of PTyr-Glu-Glu-Ile as Inhibitors of the Src SH2 Domain Binding", J. Med. Chem. (2004), 47, pp. 3131-3141.
Mitova et al., "Cyclic Peptides from a Ruegeria Strain of Bacteria Associated with the Sponge *Suberites domuncula*", J. Nat. Prod. (2004), 67, pp. 1178-1181.
Somorjai et al., "Anisotropic Rotational Diffusion and Intramolecular Motion in Cyclic Amino Acids and Peptides. An Interpretation of $^{13}C$ Spin-Lattice Relaxation Data[1a]", J. Am. Chem. Soc., 98:21 (1976), pp. 6460-6467.
Druyan et al., "Structure and Conformation of Cyclo (tri-L-Prolyl) in the Crystalline State", J. Am Chem Soc., 98:18 (1976), pp. 5496-5502.
Kessler, et al., "Peptide Conformation. Conformation of Cyclo-$(LPro_3)$ in Solution", J. Org. Chem. (1981), 46, pp. 3892-3895.
Bats et al., "Conformation and Structure of cyclo-(Dibenzylglycyl-L-proline) and cyclo-(Di-L-prolyl_D-proline) in the Crystalline State", J. Am. Chem. Soc., 102:6, (1980), pp. 2065-2070.
Madison et al., "Cyclic Peptides. IX. Conformations of a Synthetic Ion-Bonding Cyclic Peptide, cyclo-$(Pro\text{-}Gly)_3$, from Circular Dichroism and $^1H$ and $^{13}C$ Nuclear Magnetic Resonance[1]", J. Am Chem Soc., 96:21 (1974), pp. 6725-6734.
Deber et al., "Cyclic Peptides. I. Cyclo (tri-L-prolyl) and Derivatives. Synthesis and Molecular Conformation from Nuclear Magnetic Resonance", J Am. Chem. Soc, 93:19 (1971), pp. 4893-4897.
Sheehan et al., "The Synthesis of Stereochemically Pure Peptide Derivatives by the Phthaloyl Method", J. Prakt. Chem., [II] 28. 49 )1883), pp. 3822-3825.
Aposhian et al., "The in vivo Synthesis of Diethylriboflavin Phosphate", Helv. Chim. Acta, 35, 2229 (1952), pp. 6268-6369.
Wels, et al., "The Synthesis of Cyclic $(\alpha_2\beta)$-Tripeptides as Potential Peptide Turn Mimetics", Organic Letters (2002), vol. 4, No. 13, pp. 2173-2176.
Wintz et al., "A Method for the Synthesis of Cyclic Polypeptides", (1953) , Dept of Biochemistry, Yale University, New Haven, Conn., p. 3041.
Sheehan et al., "The Product Derived from the Cyclization of Triglycine Azide", (1955), Dept of Biochemistry , Yale University, New Haven, Conn., p. 6391.
Rothe et al., "Dimerization during the Cyclization of Proline Peptides", Angew. Chem. Internat. Edit., vol. 3 (1964), No. 1, p. 64.
Rothe et al., "Synthesis of Cyclotri-L-prolyl, a Cyclotripeptide Having a Nine-Membered Ring", Angew, Chem. Internat. Ed, vol. 4, (1965), No. 4, p. 356.
Davis et al., "The Cyclization of Peptides and Depsipeptides", Journal of Peptide Science (2003), 9:471-501.

* cited by examiner

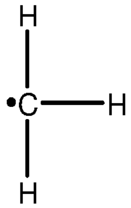
methyl
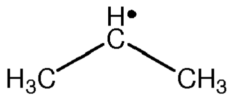
iso-propyl
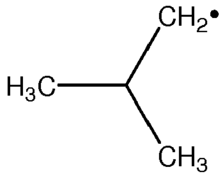
iso-butyl
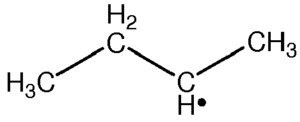
sec-butyl
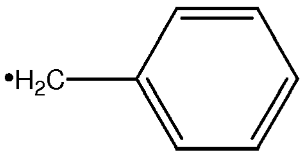
benzyl
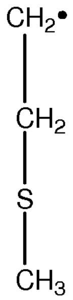
methylthio-ethyl
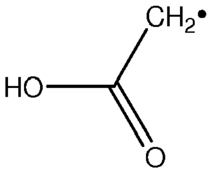
ethanoic acid
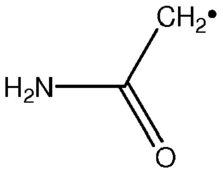
ethanoic amide
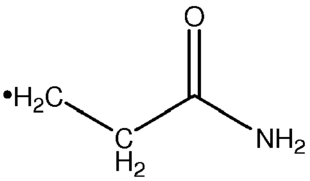
propanoic amide
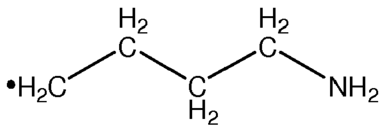
4-aminobutyl
Fig. 1 (page 1 of 2)

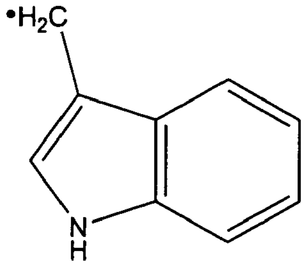
$CH_2$-linked indole
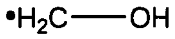
hydroxymethyl
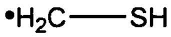
thiomethyl
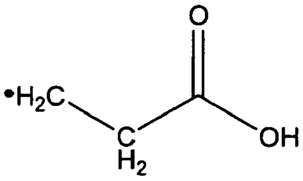
propanoic acid
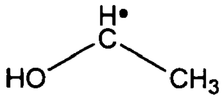
1-hydroxyethyl
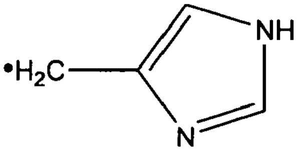
$CH_2$-linked imidazole
Fig. 1 (page 2 of 2)

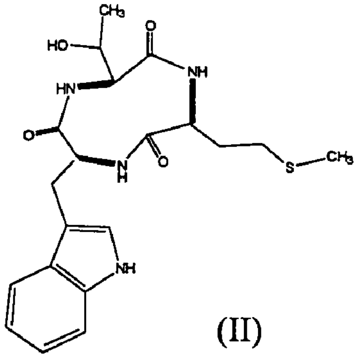
(II)
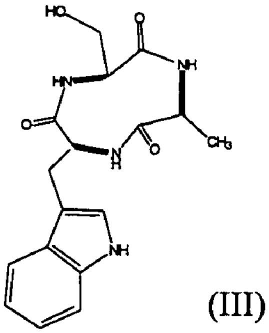
(III)
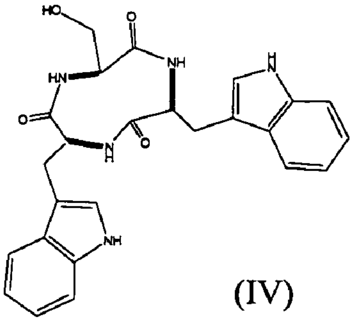
(IV)
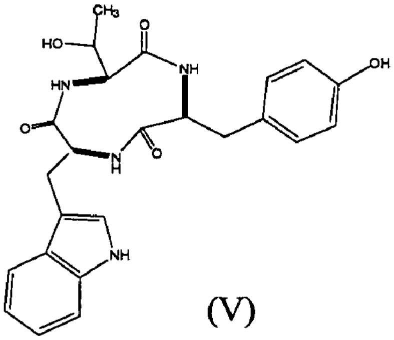
(V)
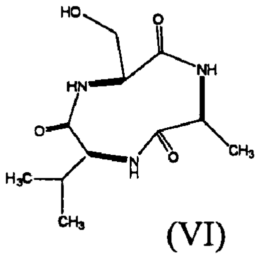
(VI)
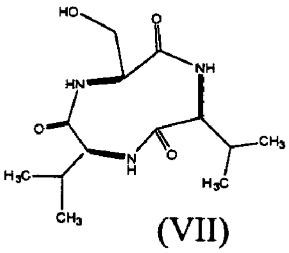
(VII)
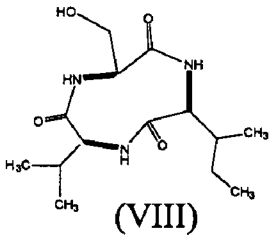
(VIII)
Fig. 2

SEQUENCE LISTING

```
<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (29)...(29)
<223> OTHER INFORMATION: n = A, G or C
<220> FEATURE:
<221> NAME/KEY: misc_feature
<222> LOCATION: (30)...(30)
<223> OTHER INFORMATION: n = A or C
<220> FEATURE:
<221> NAME/KEY: misc_feature
<222> LOCATION: (31)...(31)
<223> OTHER INFORMATION: n = T, G, or C
<220> FEATURE:
<221> NAME/KEY: misc_feature
<222> LOCATION: 32, 33, 35, 36, 38, 39
<223> OTHER INFORMATION: n = A,T,C or G

<400> SEQUENCE: 1

aagatcatat gacatcatcg tccacaacnn nnnknnknnk tgcatcagcg gcgacag        57


<210> SEQ ID NO 2
<211> LENGTH: 45
<212> TYPE: DNA
```

-continued

```
<213> ORGANISM: Artificial Sequence
<220> FEATURE:
<223> OTHER INFORMATION: synthetic oligonucleotide

<400> SEQUENCE: 2

cttgccggtg ctggccaggc tgatcaggct gtcgccgctg atgca                45
```

HETEROCYCLIC COMPOUNDS CONTAINING A NINE-MEMBERED CARBON-NITROGEN RING

CROSS-REFERENCE TO RELATED APPLICATIONS

This application claims the benefit of U.S. provisional patent application Ser. No. 60/619,420, filed Oct. 14, 2004 and is: a) a continuation-in-part of U.S. patent application Ser. No. 09/800,770, filed Mar. 6, 2001, which application claims the benefit of U.S. provisional patent application Ser. No. 60/187,130, filed Mar. 6, 2000; and; b) is a continuation-in-part of PCT application US03/27371, filed Aug. 30, 2003, which application claims the benefit of U.S. patent application Ser. No. 10/232,758, filed on Aug. 30, 2002, which applications are all incorporated herein in their entireties for all purposes.

FIELD OF THE INVENTION

The present invention relates generally to a new class of heterocyclic compounds of less than about 600 Da in molecular weight, and libraries containing the same.

BACKGROUND OF THE INVENTION

Small cyclic compounds are conformationally restricted and, as such, exhibit increased specificity and affinity in binding to other molecules, as compared to linear compounds of the same size. Further, small cyclic compounds are thought to be more stable in cells than linear compounds, and are likely to be small enough to avoid recognition by host immune system and to cross the plasma membrane of a cell (Schreiber, 2000 Science 287, 1964-1969; Scott et al., 2001 Chem. Biol. 8, 801-815). These features make small cyclic compounds very attractive drugs for the treatment of a variety of human conditions, including those caused by cancer, inflammation and infectious agents.

It follows from the above that there is a great need for new types of small cyclic compounds that are readily produced, and a great need for libraries, particularly cellular libraries, of new small cyclic compounds that can be screened to identify potent new drugs.

Current methods for making cyclic compounds, however, generally fail to meet these needs. For example, linear compounds may be cyclized in vitro (e.g., during or after chemical synthesis) by reacting the ends of the compound together to form a covalent bond therebetween. Such methods, however, are usually highly inefficient because the ends of a compound are sterically prevented from reacting. This problem is particularly exacerbated in cyclizing smaller compounds, where the ends of the compound have less choice of conformational space. Further, cyclic compounds made by cyclizing linear compounds can be difficult to purify from the linear compounds, and, as such, such methods sometimes require sophisticated purification procedures. Accordingly, despite their attractiveness as drugs, it is generally impossible to produce and purify small cyclic compounds (e.g., those less than about 600 Da) in any useful amount using synthetic chemistry.

Accordingly, there is a great need for new methods for making small cyclic compounds, as well as a great need for new small cyclic compound libraries that can be screened to identify a cyclic compound with a desired activity. The invention set forth herein meets these needs.

SUMMARY OF THE INVENTION

The present invention provides heterocyclic compounds having a nine-membered ring of three repeating C—C—N subunits covalently bound through amide bonds, and variable side groups linked to a central carbon of each subunit.

The heterocyclic compounds may be generally described by the formula:

(I)

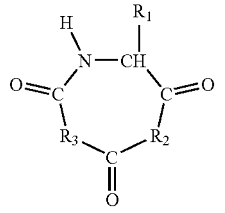

wherein $R_1$ is hydroxymethyl, 1-hydroxyethyl or thiomethyl; wherein $R_2$ and $R_3$ are, independently:

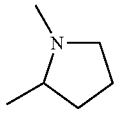

or

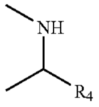

wherein $R_4$ is hydrogen, methyl, iso-propyl, iso-butyl, sec-butyl, methylthioethyl, benzyl, $CH_2$-linked 4-hydroxy-phenyl, $CH_2$-linked indole, hydroxymethyl, thiomethyl, ethanoic amide, propanoic amide, ethanoic acid, propanoic acid, 1-hydroxyethyl, 4-aminobutanyl, 4-(aminoiminomethyl)amino-propyl, hydroxymethyl, 1-hydroxyethyl, thiomethyl or $CH_2$-linked imidazole.

In certain embodiments, the invention provides compositions comprising: a pharmaceutically acceptable excipient; and a subject heterocyclic compound.

In other embodiments, the invention provides a cell comprising a subject heterocyclic compound. The cell may be a mammalian cell. The cell may also contain a nucleic acid encoding the subject heterocyclic compound. The nucleic acid encoding a subject cyclic compound may encode a fusion protein comprising, in order from N-terminus to C-terminus: a) a C-terminal intein domain; b) a linear form of the heterocyclic compound; and c) a N-terminal intein domain; wherein the fusion protein is capable of undergoing a reaction to cyclize the linear form of the heterocyclic compound to produce the heterocyclic compound. The nucleic acid may be comprised by a retroviral vector.

In particular embodiments, the invention provides a nucleic acid encoding a subject heterocyclic compound. The nucleic acid may be comprised by a retroviral vector, and may encode a nucleic acid encoding a fusion protein comprising, in order from N-terminus to C-terminus: a) a C-terminal intein domain; b) a linear form of the subject heterocyclic compound; and c) a N-terminal intein domain; wherein the fusion protein is capable of undergoing a reaction to cyclize the linear form of the cyclic compound, to produce a subject heterocyclic compound.

In certain embodiments, the invention provides a library of compounds comprising a subject heterocyclic compound. The library may comprise at least one of the heterocyclic compounds shown in FIG. 2.

In certain embodiments, the invention provides a library of polynucleotides encoding a plurality of subject heterocyclic compounds. The library may contain at least 100 or at least 1000 different heterocyclic compounds.

In particular embodiments, the invention provides a plurality of cells comprising the above-recited library of nucleic acids.

In other embodiments, the invention provides a method of screening for a bioactive cyclic compound, comprising: screening the above-recited plurality of cells for a phenotype that is not present in cells that do not contain the library of nucleic acids. The screening may include an assay to detect an inhibitor of a cancerous phenotype or may include an assay to detect an inhibitor of an infectious disease. The assay may be a cellular assay that employs an HCV IRES operably linked to a reporter.

Also described herein are cells containing the subject cyclic compounds, methods of screening those cells to identify a cyclic compound of interest, and libraries of those compounds and their encoding nucleic acids. The subject compounds may be employed in a variety of research and medical applications, including screening methods, and methods of treating a patient for hepatitis C virus (HVC) infection.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 shows molecular structures of R groups that may be employed herein.

FIG. 2 schematically shows exemplary cyclic compounds of the invention.

Figure 3:
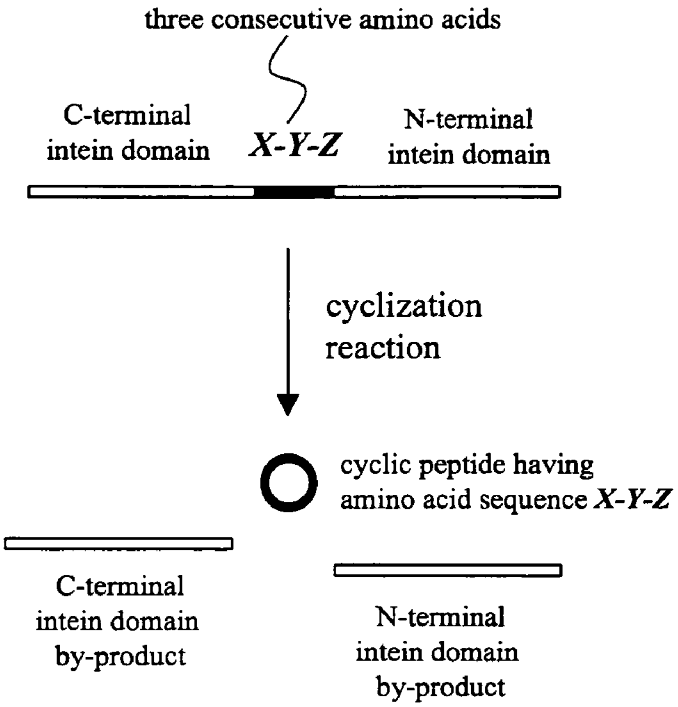
FIG. 3 schematically illustrates production of a cyclic compound of the invention.

Before the present invention is described in more detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary and preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a cyclic compound" includes a plurality of such compounds and reference to "a cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Structural representations of certain R groups described herein are shown in FIG. 1. The filled circle "●" in each of these R groups indicates the carbon atom that is linked to a member of the heterocyclic ring via a single covalent bond.

The term "cyclic compound", as used herein, refers to a cyclic compound comprising units that are covalently linked to one another by covalent bonds, typically peptide bonds. In certain embodiments, each unit comprises an amino acid, where an "amino acid" refers to a natural amino acid (i.e., a genetically coded or genetically encodable amino acid residue that is an L isomer). Thus, a cyclic compound may, in certain embodiments, is a polymer of covalently joined monomeric natural amino acids. Amino acids are sometimes referred to herein by standard one- or three-letter symbols (see, e.g., pages 58-59, "Biochemistry" Second Ed., Voet and Voet, eds. (1995) John Wiley & Sons, Inc.). In presenting the composition of a cyclic compound using a linear string of one- or three-letter symbols that denote amino acids, it is understood that the first and last amino acids of the string are covalently joined together. Since such a molecule is circular, a cyclic compound may be represented as an amino acid sequence which can be written starting at any point of the sequence. For example, a cyclic peptide having the amino acid sequence "SAW" is identical to a cyclic peptide having the sequence "AWS" or "WSA".

The terms "polypeptide" and "protein" are used interchangeably throughout the application and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline, and arginine. The side chains may be in either the (R) or the (S) configuration at the carbon bearing the amino- or carboxy-groups. Normally, the amino acids are in the (S) or L-configuration. If non-naturally occurring side chains are used, non-amino acid substituents may be used, for example to prevent or retard in vivo degradation. Naturally occurring amino acids are normally used and the protein is a cellular protein that is either endogenous or expressed recombinantly.

A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes, but is not limited to, the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

"Isolated" means that the recited material is unaccompanied by at least some of the material with which it is normally associated during synthesis (e.g., cellular components), preferably constituting at least about 0.5%, more preferably at least about 5% by weight of the total weight in a given sample. "Purified" means that the recited material comprises at least about 10% by weight of the total weight, with at least about 50% being preferred, and at least about 90% being particularly preferred.

By "inhibitory", as in the context of an "IRES-inhibitory", is meant having an activity that inhibits an activity, e.g., IRES mediated translation (i.e., rate of translation initiation by a viral or non-viral IRES). An inhibitory compound generally reduces an activity by at least 20%, e.g., at least 30%, at least 40%, at least 50%, at least 60%, at least 70%, at least 80%, at least 90%, at least 95%, up to about 99% or 100% in an assay, as compared to the same assay performed in the absence of the compound. In general, compounds of interest are those which exhibit $IC_{50}$s in a particular assay in the range of about 1 mM or less. Compounds which exhibit lower $IC_{50}$s, for example, in the range of about 100 μM, 10 μM, 1 μM, 100 nM, 10 nM, 1 nM, or even lower, are particularly useful for as therapeutics or prophylactics to treat or prevent a condition, e.g., HCV infections. Alternatively, active compounds are those which exhibit an $LD_{50}$ (i.e., concentration of compound that reduces viral titer by 50%) in the range of about 1 mM or less. Compounds which exhibit a lower $LD_{50}$, for example, in the range of about 100 μM, 10 μM, 1 μM, 100 nM, 10 nM, 1 nM, or even lower, are particularly useful for as therapeutics or prophylactics to treat or prevent any condition, for example, HCV infections.

The terms "treat", "treating", "treatment" and the like are used interchangeably herein and mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed the disease such as enhancing the effect of a viral infection. "Treating" as used herein covers treating a disease in a vertebrate and particularly a mammal and most particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

The term "effective amount", "therapeutic amount", "therapeutically effective amount" and the like are used interchangeably here to describe an amount sufficient to effect a treatment, e.g. a beneficial or desired clinical results. An effective amount can be administered in one or more administrations.

Other definitions of terms appear throughout the specification.

DETAILED DESCRIPTION OF THE INVENTION

The present invention provides heterocyclic compounds having a nine-membered ring of three repeating C—C—N subunits covalently bound through amide bonds, and variable side groups linked to a central carbon of each subunit.

The heterocyclic compounds may be generally described by the formula:

(I)

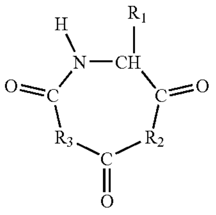

wherein $R_1$ is hydroxymethyl, 1-hydroxyethyl or thiomethyl; wherein $R_2$ and $R_3$ are, independently:

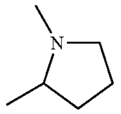

or

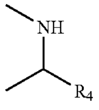

and wherein $R_4$ is hydrogen, methyl, iso-propyl, iso-butyl, sec-butyl, methylthioethyl, benzyl, $CH_2$-linked 4-hydroxyphenyl, $CH_2$-linked indole, hydroxymethyl, thiomethyl, ethanoic amide, propanoic amide, ethanoic acid, propanoic acid, 1-hydroxyethyl, 4-aminobutanyl, 4-(aminoiminomethyl) aminopropyl, hydroxymethyl, 1-hydroxyethyl, thiomethyl or $CH_2$-linked imidazole.

With the exception of hydrogen, the molecular structures of the groups that may be present as $R_4$ and $R_4$ in a subject cyclic compound are shown in FIG. 1. In each group shown in FIG. 1, the carbon atom indicated by the filled circle "●" indicate the carbon atom that is linked to a member of the 9-membered heterocyclic ring via a single covalent bond.

In certain embodiments, the subject cyclic compounds are cyclic peptides containing three amino acids. Each amino acid of the cyclic peptide is directly linked to the other two amino acids via peptide bonds, $R_1$ is a side chain of serine, threonine or cysteine and $R_4$ is a side chain of naturally occurring amino acid excluding proline. Proline is present in a subject cyclic compound if the compound contains an $R_2$ or $R_3$ represented by:

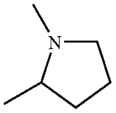

Accordingly, in certain embodiments the invention provides a cyclic compound consisting of three naturally-occurring amino acids directly linked to each other by peptide bonds. In the first amino acid position of the cyclic compound (corresponding to the amino acid that provides the $R_1$ group described above), the amino acid may be serine (providing a hydroxymethyl group), threonine (providing a 1-hydroxyethyl group) or cysteine (providing a thiomethyl group). In the second and third amino acid positions of the cyclic compound (corresponding to the amino acids that provides the $R_2$ and $R_3$ groups described above, respectively), the amino acid may, independently, be any amino acid, including glycine (providing a hydrogen group), alanine (providing a methyl group), valine (providing an iso-propyl group), leucine (providing an iso-butyl group), isoleucine (providing a sec-butyl group), methionine (providing a methylthioethyl group), phenylalanine (providing a benzyl group), tyrosine (providing a $CH_2$-linked 4-hydroxy-phenyl group), tryptophan (providing a $CH_2$-linked indole group), asparagine (providing an ethanoic amide group), glutamine (providing a propanoic amide group), aspartic acid (providing an ethanoic acid group), glutamic acid (providing a propanoic acid group), lysine (providing a 4-aminobutyl group), arginine (providing a 4-(aminoiminomethyl)aminopropyl group), histidine (providing a $CH_2$-linked imidazole group), proline (proving a straight chain $C_3H_6$ linker between a C and adjoining N of the amino acid), serine (providing a hydroxymethyl group), threonine (providing a 1-hydroxyethyl group) or cysteine (providing a thiomethyl group).

The amine bond between any two amino acids of a subject cyclic compound may be cisoid or transoid, and a cyclic compound may contain only cisoid bonds, only transoid bonds, or a mixture of the two.

Exemplary cyclic compounds of the invention are shown in FIG. 2. These cyclic compounds were identified as having anti-HCV activity in a cellular screening assay that involves: producing a library of cyclic compounds in mammalian cells using an intein system (similar to that described by Kinsella et al. J Biol Chem. 2002 277:37512-8), and determining whether those cyclic compounds decrease expression of an IRES-regulated reporter protein. Accordingly, the subject compounds may be used to treat infection of viruses that contain an IRES, notably Hepatitis C virus (HCV).

Also described herein are cells containing cyclic compounds of the invention, methods of screening those cells to identify a cyclic compound of interest, and libraries of the compounds and their encoding nucleic acids.

As will be described in greater detail below, a cyclic compound may be made using an intein based system, either in a cell (e.g., a bacterial or mammalian cell) or using a cell-free system (i.e., "in vitro"). Accordingly, a cyclic compound may be present in a cell or may be isolated from a cell and in certain cases may be purified. If the cyclic compound is isolated, it may be present in pharmaceutically-acceptable excipient. If the cyclic compound is present in a cell, it may be present along with other components required for its synthesis, such as its encoding nucleic acids, or the fusion polypeptide encoded by those nucleic acids. In other embodiments, the compound is present in a cell because it has been contacted with a cell and has entered the cell.

In particular embodiments, a subject cyclic compound may be part of a compound library that may be employed in methods of screening for compounds having a desirable activity. A subject compound library may contain at least 10, at least 100, at least 1000 or at least 10,000 different compounds, usually up to about $10^7$, $10^8$ or $10^9$ or more different compounds, and may contain at least 1, at least 5, at least 10, at least 20, at least 50, at least 100, at least 400, at least 1000 or more, usually up to about 1200, of the instant cyclic compounds. As will be discussed in greater detail below, since the compounds may be made in a cell, one aspect of the present invention is a library that is a library of cells, i.e., a cellular library, containing a plurality of cyclic compounds of the invention. The cells of the library may contain the subject cyclic compounds, nucleic acids encoding those compounds, or the fusion proteins encoding by those nucleic acids. In certain embodiments, the library may contain all of the cyclic compounds encompassed by the formula set forth above, or their encoding nucleic acids. In certain embodiments, a subject library may contain at least one of the compounds shown in FIG. 2, or a nucleic acid encoding that compound.

As mentioned above and as discussed in greater detail below, a cyclic compound of the invention may be made using an intein system. In general, such methods involve producing a fusion protein containing, in order from N-terminus to C-terminus: a) a C-terminal intein domain; b) a linear form of a subject cyclic compound; and c) a N-terminal intein domain. The fusion protein is capable of undergoing a reaction to cyclize the linear form of the cyclic compound to produce the cyclic compound. This reaction may occur in vitro (in a cell-free system) or in a cell using known conditions. FIG. 3 illustrates this reaction. The reaction produces three products: the cyclic compound, and the two intein domain by-products.

The intein systems that may be employed in the subject methods are capable of protein splicing in trans or cis. Such inteins are well known in the art and are reviewed in a number of publications, including Paulus (Annual Review of Biochemistry, 2000, 69: 447-496), Paulus (Chemical Society Reviews 1998 27:375-386), Paulus (Bioorganic Chemistry 2001 29:119-129) and published U.S. patent applications 20040014100 and 20030013148. A comprehensive list of inteins that may be employed to make the subject cyclic compounds and description of their biology is found at New England Biolabs Intein Database (InBase Reference: Perler, F. B. (2002). InBase, the Intein Database. Nucleic Acids Res. 30, 383-384), as found at the world wide website of New England Biolabs.

Accordingly and without intending to limit the invention to any particular intein, exemplary inteins for use in the subject methods include: the Ssp DnaB intein from *Synechocystis* spp. strain PCC6803, the Mxe GyrA intein from *Mycobacterium xenopi*, the CIV RIR1 intein from Chilo iridescent virus, the Ctr VMA intein from *Candida tropicalis*, the Gth DnaB intein from *Guillardia theta*, the Ppu DnaB intein from *Porphyra purpurea*, the Sce VMA intein from *Saccharomyces cerevisiae*, the Mfl RecA intein from *Mycobacterium flavescens*, the Ssp DnaE intein from *Synechocystis* spp. strain PCC6803, the Mle DnaB intein from *Mycobacterium leprae*, the Mja KIbA intein from *Methanococcus jannaschii*, the Pfu KIbA from *Pyrococcus furiosus*, the Mth RIR1 intein from *Methanobacterium thermoautotrophicum* (delta H strain), the Pfu RIR1-1 intein from *Pyrococcus furiosus*, the Psp-GBD Pol intein from *Pyrococcus* spp. the GB-D, Thy Pol-2 intein from *Thermococcus hydrothermalis*, the Pfu IF2 intein from *Pyrococcus furiosus*, Pho Lon intein from *Pyrococcus horikoshii* OT3, the Mja r-Gyr intein from *Methanococcus jannaschii*, the Pho RFC intein from *Pyrococcus horikoshii* OT3, the Pab RFC-2 intein from *Pyrococcus abyssi*, the Mja RtcB (Mja Hyp-2) intein from *Methanococcus jannaschii*, the Pho VMA intein from *Pyrococcus horikoshii* OT3, the Mtu RecA intein, the PI-pfuI intein and the PU-pfu II intein, and artificial trans-splicing variants thereof.

As is well recognized in the art, inteins are typically composed of two domains (termed herein the "N-terminal domain" and "C-terminal domain") that can be naturally (in the case of the Ssp DnaE intein, for example) or non-naturally (i.e., artificially or by recombinant means, for example) present as two different molecules. These intein domains, when present together, can reconstitute an active intein, and can be used to join two different polypeptides together in trans or in cis. Also as well recognized in the art, inteins may be used to produce compounds other than those described herein in vivo and in vitro. Such methods are generally described in published U.S. patent application 20040014100, Camarero and Muir (J. Am. Chem. Soc. 1999 121:5597-5598), Iwai and Pluckthun (FEBS Lett. 1999 459:166-172), Evans, et al. (J. Biol. Chem. 1999 274:18359-18363) and Scott et al. (Proc. Natl. Acad. Sci. 1999 96:13638-13643). Any intein may be used to make a subject cyclic compound.

Naturally-occurring intein-mediated protein splicing proceeds according to one of two pathways, a classical and alternative pathway depending on which particular intein is used. Naturally-occurring inteins that catalyze splicing using the classical pathway, such as many of those listed above, typically contain a N-terminal cys or ser amino acid as an intein reactive site. Naturally-occurring inteins that catalyze splicing using the alternative pathway, such as the *M. jannaschii* KlbA intein, and others, typically use a N-terminal ala amino acid as an intein reactive site. Almost all naturally-occurring inteins contain a ser, cys or thr amino acid as a C-terminal intein reactive site. Accordingly, in performing the subject methods, a wide variety of inteins may be used. Depending on the intein used for its synthesis, the resulting cyclic compound almost invariably contains a cys, ser or thr at one or more positions.

A fusion protein used in the present invention may be encoded by a nucleic acid, and that nucleic acid is introduced into a cell to produce the fusion protein. In many embodiments, the subject compound is produced in the cell. In certain embodiments, however, the fusion protein is purified from the cell in order to produce the cyclic compound in vitro.

In general, the subject cyclic compounds may be made in a cell or in vitro using well known intein-based methods that have been successfully applied to the synthesis of other cyclic compounds. For example, U.S. patent application 20040014100, Camarero and Muir (J. Am. Chem. Soc. 1999 121:5597-5598), Iwai and Pluckthun (FEBS Lett. 1999 459: 166-172), Evans, et al. (J. Biol. Chem. 1999 274:18359-18363); Scott et al. (Proc. Natl. Acad. Sci. 1999 96:13638-13643), U.S. patent application Ser. No. 09/800,770 (filed Mar. 6, 2001) and Kinsella et al. (J. Biol. Chem. 2002 277: 37512-8) each describe intein based methods that are readily adapted to produce the instant compounds. Accordingly, the invention provides a method of making a subject cyclic compound.

A mentioned above, a subject cyclic compound is usually produced using a nucleic acid encoding an intein fusion protein containing, in order, from N to C: a) a C-terminal intein domain; b) a linear form of a subject cyclic compound; and c) a N-terminal intein domain. This nucleic acid produces a subject cyclic compound upon its introduction into a cell, and, as such, the nucleic acid encodes the cyclic compound. Accordingly, the invention further provides nucleic acids encoding a cyclic compound of the invention, and libraries thereof.

In certain embodiments, heterocyclic compounds containing proline or glycine may be excluded from the invention described herein. In other words, in certain embodiments the subject heterocyclic compounds may be generally described by the formula:

(I)

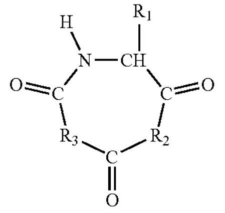

wherein $R_1$ is hydroxymethyl, 1-hydroxyethyl or thiomethyl; and wherein $R_2$ and $R_3$ are, independently:

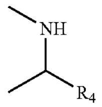

and wherein $R_4$ is methyl, iso-propyl, iso-butyl, sec-butyl, methylthioethyl, benzyl, $CH_2$-linked 4-hydroxy-phenyl, $CH_2$-linked indole, hydroxymethyl, thiomethyl, ethanoic amide, propanoic amide, ethanoic acid, propanoic acid, 1-hydroxyethyl, 4-aminobutanyl, 4-(aminoiminomethyl)aminopropyl, hydroxymethyl, 1-hydroxyethyl, thiomethyl or $CH_2$-linked imidazole.

The subject compounds and libraries thereof may be employed in a variety of methods, including methods of screening for drugs having a low molecular weight (i.e., drugs that are less than about 600 Da). In particular embodiments, the subject compounds may be tested for modulation (i.e., inhibition or an increase) of any aspect of animal (e.g., human) health, including, for example, any aspect of cancer, infectious disease or inflammation.

Formulations and Routes of Administration

The compounds described herein can be formulated in a variety of ways suitable for administration. In general, these compounds are provided in the same or separate formulations in combination with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the agents are formulated separately or in combination, e.g., in an aqueous or non-aqueous formulation, which may further include a buffer. Suitable aqueous buffers include, but are not limited to, acetate, succinate, citrate, and phosphate buffers varying in strength from 5 mM to 100 mM. In some embodiments, the aqueous buffer includes reagents that provide for an isotonic solution. Such reagents include, but are not limited to, sodium chloride, and sugars e.g., mannitol, dextrose, sucrose, and the like. In some embodiments, the aqueous buffer further includes a non-ionic surfactant such as polysorbate 20 or 80.

Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In the subject methods, the active agents may be administered to the host using any convenient means capable of resulting in the desired therapeutic effect. Thus, the agents can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, agents may be administered in the form of their pharmaceutically acceptable salts, or they may also be used alone or in appropriate association, as well as in combination, with other pharmaceutically active compounds. The following methods and excipients are merely exemplary and are in no way limiting.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature. Agents can also be provided in sustained release or controlled release formulations, e.g., to provide for release of agent over time and in a desired amount (e.g., in an amount effective to provide for a desired therapeutic or otherwise beneficial effect).

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of the agents calculated in an amount sufficient to produce the desired effect in association with a pharmaceutically acceptable diluent, carrier or vehicle. The specifications for the unit dosage forms for use in the present invention depend on the particular compound employed and the effect to be achieved, the pharmacodynamics associated with each compound in the host, and the like.

Dosage forms of particular interest include those suitable to accomplish intravenous or oral administration, as well as dosage forms to provide for delivery by a nasal or pulmonary route (e.g., inhalation), e.g., through use of a metered dose inhaler and the like.

In general, agents for use in the invention is formulated in either parenteral or enteral forms, usually enteral formulations, more particularly oral formulations. Agents for use in the invention are formulated for parenteral administration, e.g., by subcutaneous, intradermal, intraperitoneal, intravenous, or intramuscular injection. Administration may also be accomplished by, for example, enteral, oral, buccal, rectal, transdermal, intratracheal, inhalation (see, e.g., U.S. Pat. No. 5,354,934), etc.

Methods of Using the Subject Cyclic Compounds

The subject cyclic compounds are readily employed in screening assays to identify biologically active compounds. In certain embodiments, since the compounds may be produced in a cell using an intein system, the method employed may be a cellular assay. The cellular assay may involve producing a subject cyclic compound in a cell, and determining the effect of the compound on an activity of the cell. In certain embodiments, the cell may contain a reporter protein that provides a means for evaluating an activity of the cell. However, a number of other assays, including cell viability or cell proliferation assays, or assays to evaluate the infectivity and/or replication of an infective agent (e.g., a virus such as HCV) may be employed. In one embodiment, the method employed is a cellular assay and uses a reporter system to provide a read out on IRES-inhibitory activity of the cyclic compound.

As mentioned above, in certain embodiments, the screening methods may be performed in a cellular environment. The cell may be in vitro (e.g., a cultured cell), ex vivo (e.g., in an intact organ removed from a mammalian subject such as a removed liver), or in vivo (e.g., an animal model for a viral infection, e.g, an animal model for HCV, or in a mammalian subject). The cyclic compound-encoding nucleic acids may be introduced into a cell using a variety of means, including transfection by a retroviral vector, or by contacting the cell with the compound.

The invention also provides a method of inhibiting viral replication in a virus-infected cell. In general, these methods involve contacting a cell with a subject cyclic compound in an amount effective to inhibit viral replication in the cell.

The invention further provides methods for inhibiting viral IRES-mediated translation. These methods generally involve contacting a viral IRES with an IRES-inhibitory cyclic compound, in an amount effective to inhibit translation mediated by the IRES. In certain embodiments, the methods involve contacting a cell infected with an IRES containing virus or a model thereof, e.g., HCV or model thereof (e.g., an HCV subgenomic replicon; Lim, Virology. 2002 303(1):79-99), with an above-described cyclic compound, and inhibiting viral replication. Again, the cell may be a cell in vitro, ex vivo or in vivo.

In certain embodiments, the subject methods may involve inhibiting HCV replication in replicon cells. HCV replication assays in which the subject compounds may be employed are described in Lohmann et al (1999 Science 258:110-113), WO03/040112 and WO2004018463. Other embodiments may employ an HCV infection and replication assays, as described in Fournier et al, (1998 J. Gen. Virol. 79:2367-2374).

In general, a cyclic compound described above will reduce viral replication by up to about 20%, up to about 30%, up to about 40%, up to 50%, up to about 80%, up to about 90% or up to about 95% or more, using a standard replicon colony formation assay, as compared to controls in the absence of an agent.

In some embodiments of the invention a subject cyclic compound is contacted with a cell that is already infected with a virus, or, in certain other embodiments, an cyclic compound is contacted with a cell before its infection with a virus. In these embodiments, the subject compound may be administered as a prophylactic, e.g., to increase the viability of a cell and provide "protection" of a cell against a future viral infection or to protect a normal transplanted liver from a virus in a host, for example.

In any of the above methods, the virus or replicon thereof may be any virus containing an IRES, including *Flaviviridae* viruses, e.g., HCV.

Certain of the above-methods may be performed on a non-human animal model for the virus. Many such animal models using mammals, especially of mouse, monkeys, rats, cats, dogs, guinea pigs, chimpanzees, etc., are known to one of skill in the art. Mouse models, in particular the mouse models for HCV, described in PCT publication WO01/67854, may be used. Other models include those described in WO 99/16307 and Galun et al; *J. Infect. Dis.* 172:25-30 (1995), describing transplantation of HCV-infected human hepatocytes into liver of immunodeficient mice; Bronowicki et al. *Hepatology* 28:211-8 (1998), describing intraperitoneal injection of HCV-infected hematopoietic cells into SCID mice; and Lerta et al. *Hepatology* 28(4Pt2):498A (1998), describing mice transgenic for the HCV genome.

In many embodiments, upon administration of a subject agent, a symptom (e.g. viability of pathogen infected cells, lesions, bleeding, bruising, titer, ALT, the number of infected cells) of the pathogen exhibited by the animal is reduced up to 20%, up to 50%, up to 70%, up to 80%, up to 90%, up to 95%, up to 98%, and even up to 99% or 99.5% as compared to an animal that is not administered a subject agent. In other embodiments, upon administration of a subject agent, a symptom (e.g. CD4 count, ALT or HAAT activity, etc.) of the pathogen exhibited by the animal is increased up to 20%, up to 50%, up to 70%, up to 80%, up to 90%, up to 95%, up to 98%, and even up to 99% or 99.5%, as compared to an animal that is not administered a subject agent.

In many embodiments, a blood sample is taken from the animal and tested for the level of a blood product, such as a virus, cell, a protein, or a molecule (e.g. viral titer, viral genome, viral mRNA, CD4 count or HAAT activity etc.). In other embodiments, a sample of tissue is taken from the test animal and symptoms (e.g. cell death, lesions, viral titer etc) are measured. Thus, generally, the present invention provides methods for generating libraries of cyclic peptides using inteins. Inteins are self-splicing proteins that occur as in-frame insertions in specific host proteins. In a self-splicing reaction, inteins excise themselves from a precursor protein, while the flanking regions, the exteins, become joined via a new peptide bond to form a linear protein. By changing the N to C terminal orientation of the intein segments, the ends of the extein join to form a cyclized extein.

In addition, the invention provides methods for identifying cyclic peptides that prevent or alter the interaction of interacting proteins and the use of such peptides. Generally, the method includes providing a cyclic peptide formed from an intein catalyzed reaction. Preferably, the cyclic peptide alters association of interacting proteins. In addition, the invention provides identifying the cyclic peptide that modulates interaction of interacting proteins. The cyclic peptide finds use as a drug or drug mimetic. Preferably, the cyclic peptide causes an alteration in ubiquitination of a molecule.

Because intein function is not strongly influenced by the nature of the extein polypeptide sequences located between them, standard recombinant methods can be used to insert random libraries into this position. Placement of these intein libraries into any number of delivery systems allows for the subsequent expression of unique cyclic peptides within individual cells. Such cells can then be screened to identify peptides of interest.

Accordingly, the present invention provides fusion polypeptides comprising intein motifs and peptides.

By "fusion polypeptide" or "fusion peptide" or grammatical equivalents herein is meant a protein composed of a plurality of protein components, that while typically unjoined in their native state, are joined by their respective amino and carboxyl termini through a peptide linkage to form a single continuous polypeptide. "Protein" in this context includes proteins, polypeptides and peptides. Plurality in this context means at least two, and preferred embodiments generally utilize two components. It will be appreciated that the protein components can be joined directly or joined through a peptide linker/spacer as outlined below. In addition, as outlined below, additional components such as fusion partners including targeting sequences, etc. may be used.

The present invention provides fusion proteins of intein motifs and random peptides. By "inteins", or "intein motifs", or "intein domains", or grammatical equivalents herein is meant a protein sequence which, during protein splicing, is excised from a protein precursor. Also included within in the definition of intein motifs are DNA sequences encoding inteins and mini-inteins.

Many inteins are bifunctional proteins mediating both protein splicing and DNA cleavage. Such elements consist of a protein splicing domain interrupted by an endonuclease domain. Because endonuclease activity is not required for protein splicing, mini-inteins with accurate splicing activity can be generated by deletion of this central domain (Wood et al., Nature Biotechnology, 17:889-892 (1999); hereby incorporated by reference).

Protein splicing involves four nucleophilic displacements by three conserved splice junction residues. These residues, located near the intein/extein junctions, include the initial cysteine, serine, or threonine of the intein, which intiates splicing with an acyl shift. The conserved cysteine, serine, or threonine of the extein, which ligates the exteins through nucleophilic attack, and the conserved C-terminal histidine and asparagine of the intein, which releases the intein from the ligated exteins through succinimide formation. See Wood, et al., supra.

Inteins also catalyze a trans-ligation reaction. The ability of intein function to be reconstituted in trans by spatially separated intein domains suggests that reorganization of the self-splicing motifs can be used to produce peptides with a circular topology.

In a preferred embodiment, the translational order in which the N- and C-terminal intein motifs are normally synthesized within a polypetide chain is reversed. Generally, a reversal in the translational order in which the N- and C-terminal intein motifs are synthesized should not fundamentally change the enzymatic function of the intein. However, the location of the intervening peptide's amino and carboxy termini are altered in such a way that the product of the intein ligation reaction is no longer linear, but rather is cyclized. To effectively express unique peptides in cells, fusion polypetides comprising a C-terminal motif, a peptide and a N-terminal motif are selected or designed for the production of random libraries of cyclic peptides in vivo.

In a preferred embodiment, the fusion polypeptide is designed with the primary sequence from the N-terminus comprising $I_A$-target-$I_B$. $I_A$ is defined herein as the C-terminal intein motif, $I_B$ is defined herein as the N-terminal intein motif and target is defined herein as a peptide. DNA sequences encoding the inteins may be obtained from a prokaryotic DNA sequence, such as a bacterial DNA sequence, or a eukaryotic DNA sequence, such as a yeast DNA sequence. The Intein Registry includes a list of all experimental and theoretical inteins discovered to date and submitted to the registry(see the website of New England Biolabs).

In a preferred embodiment, fusion polypeptides are designed using intein motifs selected from organisms belonging to the Eucarya and Eubacteria, with the intein Ssp DnaB (GenBank accession number Q55418) being particularly preferred. The GenBank accession numbers for other intein proteins and nucleic acids include, but are not limited to: Ceu ClpP (GenBank acession number P42379); CIV RIR1 (T03053); Ctr VMA (GenBank accession number A46080); Gth DnaB (GenBank accession number 078411); Ppu DnaB (GenBank accession number P51333); Sce VMA (GenBank accession number PXBYVA); Mfl RecA (GenBank accession number not given); Mxe GyrA (GenBank accession number P72065); Ssp DnaE (GenBank accession number S76958 & S75328); and Mle DnaB (GenBank accession number CAA17948.1)

In other embodiments, inteins with alternative splicing mechanisms are preferred (see Southworth et al., EMBO J., 19:5019-26 (2000)). The GenBank accession numbers for inteins with alternative splicing mechanisms include, but are not limited to, Mja K1bA (GenBank accession number Q58191) and Pfu K1bA (PF__949263 in UMBI).

In yet other embodiments, inteins from thermophilic organisms are used. Random mutagenesis or directed evolution (e.g., PCR shuffling, etc.) of inteins from these organisms could lead to the isolation of temperature sensitive mutants. Thus, inteins from thermophiles (e.g., Archaea) which find use in the invention are: Mth RIR1 (GenBank accession number G69186); Pfu RIR1-1 (AAB36947.1); Psp-GBD Pol (GenBank accession number AAA67132.1); Thy Pol-2 (GenBank accession number CAC18555.1); Pfu IF2 (PF__1088001 in UMBI); Pho Lon Baa29538.1); Mja r-Gyr (GenBank accession number G64488); Pho RFC (GenBank accession number F71231); Pab RFC-2 (GenBank accession number C75198); Mja RtcB (also referred to as Mja Hyp-2; GenBank accession number Q58095); and Pho VMA (NT01PH1971 in Tigr).

Preferred fusion polypeptides of the invention increase the efficiency of the cyclization reaction by selecting or designing intein motifs with altered cyclization activity when expressed in vivo. In a preferred embodiment, the fusion polypeptides of the invention employ the DNA sequence encoding the *Synechocystis* ssp. strain PCC6803 DnaB intein.

In a preferred embodiment, fusion polypeptides are designed using mutant intein sequences with altered cyclization activity as described below. In addition, preferred mutant intein sequences are set forth in U.S. patent application Ser. No. 10/197,927, filed Jul. 16, 2002, which is expressly incorporated herein by reference.

In a preferred embodiment, the fusion polypeptides of the invention comprise random peptides. By "random peptides" herein is meant that each peptide consists of essentially random amino acids. Since generally these random peptides (or nucleic acids, discussed below) are chemically synthesized, they may incorporate any amino acid at any position. The synthetic process can be designed to generate randomized proteins to allow the formation of all or most of the possible combinations over the length of the sequence, thus forming a library of randomized peptides.

The fusion polypeptide preferably includes additional components, including, but not limited to, reporter proteins and fusion partners.

In a preferred embodiment, the fusion polypeptides of the invention comprise a reporter protein. By "reporter protein" or grammatical equivalents herein is meant a protein that by its presence in or on a cell or when secreted in the media allow the cell to be distinguished from a cell that does not contain the reporter protein. As described herein, the cell usually comprises a reporter gene that encodes the reporter protein.

Reporter genes fall into several classes, as outlined above, including, but not limited to, detection genes, indirectly detectable genes, and survival genes.

As is known in the art, there are a variety of autofluorescent proteins known; these generally are based on the green fluorescent protein (GFP) from *Aequorea* and variants thereof; including, but not limited to, GFP, (Chalfie et al., "Green Fluorescent Protein as a Marker for Gene Expression," Science 263(5148):802-805 (1994)); enhanced GFP (EGFP; Clontech—Genbank Accession Number U55762)), blue fluorescent protein (BFP; Quantum Biotechnologies, Inc., 1801 de Maisonneuve Blvd. West, 8th Floor, Montreal (Quebec) Canada H3H 1J9; Stauber, R. H., Biotechniques 24(3): 462-471 (1998); Heim, R. and Tsien, R. Y. Curr. Biol. 6:178-182 (1996)), enhanced yellow fluorescent protein (EYFP; Clontech Laboratories, Inc., Palo Alto, Calif.) and red fluorescent protein. In addition, there are recent reports of autofluorescent proteins from *Renilla* and *Ptilosarcus* species. See WO 92/15673; WO 95/07463; WO 98/14605; WO 98/26277; WO 99/49019; U.S. Pat. Nos. 5,292,658; 5,418,155; 5,683,888; 5,741,668; 5,777,079; 5,804,387; 5,874,304; 5,876,995; and 5,925,558; all of which are expressly incorporated herein by reference.

In a preferred embodiment, the reporter protein is a survival protein. By "survival protein", "selection protein" or grammatical equivalents herein is meant a protein without which the cell cannot survive, such as drug resistance genes. As described herein, the cell usually does not naturally contain an active form of the survival protein which is used as a scaffold protein. As further described herein, the cell usually comprises a survival gene that encodes the survival protein.

The expression of a survival protein is usually not quantified in terms of protein activity, but rather recognized by conferring a characteristic phenotype onto a cell which comprises the respective survival gene or selection gene. Such survival genes may provide resistance to a selection agent (e.g., an antibiotic) to preferentially select only those cells which contain and express the respective survival gene. The variety of survival genes is quite broad and continues to grow (for review see Kriegler, Gene Transfer and Expression: A Laboratory Manual, W.H. Freeman and Company, New York, 1990). Typically, the DNA containing the resistance-conferring phenotype is transfected into a cell and subsequently the cell is treated with media containing the concentration of drug appropriate for the selective survival and expansion of the transfected and now drug-resistant cells.

Selection agents such as ampicillin, kanamycin and tetracycline have been widely used for selection procedures in prokaryotes (e.g., see Waxman and Strominger, Annu. Rev. Biochem. 52:825-69 (1983); Davies and Smith, Annu. Rev. Microbiol. 32:469-518 (1978); and Franklin, Biochem J., 105(1):371-8 (1967)). Suitable selection agents for the selection of eukaryotic cells include, but are not limited to, blasticidin (Izumi et al., Exp. Cell Res. 197(2):229-33 (1991); Kimura et al., Biochim. Biophys. Acta 1219(3):653-9 (1994); Kimura et al., Mol. Gen. Genet. 242(2):121-9 (1994)), histidinol D (Hartman and Mulligan, Proc. Natl. Acad. Sci. USA. 85(21):8047-51 (1988)), hygromycin (Gritz and Davies, Gene 25(2-3):179-88 (1983); Sorensen et al., Gene 112(2):257-60 (1992)), neomycin (Davies and Jimenez, Am. J. Trop. Med. Hyg., 29(5 Suppl):1089-92 (1980); Southern and Berg, J. Mol. Appl. Genet. 1(4):327-41 (1982)), puromycin (de la Luna et al., Gene 62(1):121-6 (1988)) and bleomycin/phleomycin/zeocin antibiotics (Mulsant et al., Somat Cell. Mol. Genet. 14(3):243-52 (1988)).

Survival genes encoding enzymes mediating such a drug-resistant phenotype and protocols for their use are known in the art (see Kriegler, supra). Suitable survival genes include, but are not limited to, thymidine kinase (TK; Wigler et al., Cell 11:233 (1977)), adenine phosphoribosyltransferase (APRT; Lowry et al., Cell 22:817 (1980); Murray et al., Gene 31:233 (1984); Stambrook et al., Som. Cell. Mol. Genet. 4:359 (1982)), hypoxanthine-guanine phosphoribosyltransferase (HGPRT; Jolly et al., Proc. Natl. Acad. Sci. USA 80:477 (1983)), dihydrofolate reductase (DHFR; Subramani et al., Mol. Cell. Biol. 1:854 (1985); Kaufman and Sharp, J. Mol. Biol. 159:601 (1982); Simonsen and Levinson, Proc. Natl. Acad. Sci. USA. 80:2495 (1983)), aspartate transcarbamylase (Ruiz and Wahl, Mol. Cell. Biol. 6:3050 (1986)), ornithine decarboxylase (Chiang and McConlogue, Mol. Cell. Biol. 8:764 (1988)), aminoglycoside phosphotransferase (Southern and Berg, Mol. Appl. Gen. 1:327 (1982); Davies and Jiminez, supra)), hygromycin-B-phosphotransferase (Gritz and Davies, supra; Sugden et al., Mol. Cell. Biol. 5:410 (1985); Palmer et al., Proc. Natl. Acad. Sci. USA 84:1055 (1987)), xanthine-guanine phosphoribosyltransferase (Mulligan and Berg, Proc. Natl. Acad. Sci. USA 78:2072 (1981)), tryptophan synthetase (Hartman and Mulligan, Proc. Natl. Acad. Sci. USA 85:8047 (1988)), histidinol dehydrogenase (Hartman and Mulligan, supra), multiple drug resistance biochemical marker (Kane et al., Mol. Cell. Biol. 8:3316 (1988); Choi et al., Cell 53:519 (1988)), blasticidin S deaminase (Izumi et al., Exp. Cell. Res. 197(2):229-33 (1991)), bleomycin hydrolase (Mulsant et al., supra), and puromycin-N-acetyl-transferase (Lacalle et al., Gene 79(2):375-80 (1989)), By "fusion partner" herein is meant a sequence that is associated with the fusion polypeptide that confers upon all members of the library in that class a common function or ability. Fusion partners can be heterologous (i.e., not native to the host cell), or synthetic (i.e., not native to any cell). Suitable fusion partners include, but are not limited to: a) targeting sequences, defined below, which allow the localization of the peptide into a subcellular or extracellular compartment; b) rescue sequences as defined below, which allow the purification or isolation of either the peptides or the nucleic acids encoding them; or c), any combination of a) and b).

In a preferred embodiment, the invention provides libraries of fusion polypeptides. By "library" herein is meant a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is of interest. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as proposed here for expression in retroviruses, has the potential to code for $20^7$ ($10^9$) to $20^{20}$. Thus, with libraries of $10^7$ to $10^8$ per ml of retroviral particles the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different expression products are simultaneously analyzed in the subject methods. Preferred methods maximize library size and diversity.

In a preferred embodiment, libraries of all combinations of a peptide 3 to 30 amino acids in length are synthesized and analyzed as outlined herein. Libraries of smaller peptides, i.e., 3 to 4 amino acids in length, are advantageous because they are more constrained and this there is a better chance that these libraries possess desirable pharmocokinetics properties as a consequence of their smaller size. Accordingly, the libraries of the present invention may be one of any of the following lengths: 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids and 30 amino acids in length.

In some embodiments the library is random, i.e., all combinations of a peptide of a given length are encoded. However, in other alternative embodiments, the library is biased as set forth below.

Using the nucleic acids of the present invention which encode a fusion protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The fusion nucleic acids are introduced into cells to screen for cyclic peptides capable of altering the phenotype of a cell. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The fusion nucleic acids may stably integrate into the genome of the host cell (for example, with retroviral introduction, outlined below), or may exist either transiently or stably in the cytoplasm (e.g., through the use of traditional plasmids, utilizing standard regulatory sequences, selection markers, etc.). As many pharmaceutically important screens require human or model mammalian cell targets, retroviral vectors capable of transfecting such targets are preferred.

In a preferred embodiment, the fusion nucleic acids are part of a retroviral particle which infects the cells. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

In a preferred embodiment, the fusion nucleic acids are introduced into cells using retroviral vectors. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153-159 (1993), hereby incorporated by reference). Such helper-defective packaging lines are capable of producing all the necessary trans proteins—gag, pol, and env—that are required for packaging, processing, reverse transcription, and integration of recombinant genomes. Those RNA molecules that have in cis the 5 packaging signal are packaged into maturing virions. Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al., supra: Pear et al., Proc. Natl. Acad. Sci. USA 90(18):8392-6 (1993); Kitamura et al., Proc. Natl. Acad. Sci. USA 92:9146-9150 (1995); Kinsella et al., Human Gene Therapy 7:1405-1413 (1996); Hofmann et al., Proc. Natl. Acad. Sci. USA 93:5185-5190 (1996); Choate et al., Human Gene Therapy 7:2247 (1996); and WO 94/19478; and references cited therein, all of which are incorporated by reference.

In one embodiment of the invention, the library is generated in a intein-catalyzed cyclization scaffold. By "intein-catalyzed cyclization scaffold" herein is meant that the intein is engineered such that a cyclic peptide is generated upon intein-mediated splicing of the extein-intein junction points. Preferably, an intein cyclization scaffold includes the C-terminal intein motif, a library insert of 3 amino acids in length, and the N-terminal intein motif. The C- and N-terminal intein motifs can be derived from any number of known inteins capable mediating protein splicing, including split-inteins.

Most wild-type inteins have requirements for a specific extein-encoded amino acid at the C-intein (IntB)/C-extein junction point. This varies depending on the intein, but most often consists of an cysteine, threonine or serine. Intein-generated cyclic peptide libraries may be generated in which this particular amino acid is fixed and corresponds to the amino acid present in the wild-type sequence. For example, the Ssp. DnaB intein utilizes an extein-encoded serine in this position.

A number of inteins have the ability to catalyze protein splicing when non-native amino acids are substituted at the C-intein (IntB)/C-extein junction point position. Degeneracy at the C-intein (IntB)/C-extein junction point position leads to cyclic peptide libraries of greater complexity and therefore added utility. The proposed degeneracy in this position most likely consists of a cysteine, serine or threonine but is not limited to these amino acids. The ability of a given intein-catalyzed cyclization scaffold to tolerate degeneracy at this position depends on the specific intein utilized and it's mechanism of protein splicing. Thus, isolation of intein cyclization scaffolds with a greater tolerance for degeneracy at the C-intein (IntB)/C-extein junction point is within the scope of this invention.

In one embodiment of the invention, the library is generated in a retrovirus DNA construct backbone, as is generally described in U.S. Ser. No. 08/789,333, filed Jan. 23, 1997, incorporated herein by reference. Standard oligonucleotide synthesis is done to generate the random portion of the candidate bioactive agent, using techniques well known in the art (see Eckstein, Oligonucleotides and Analogues, A Practical Approach, IRL Press at Oxford University Press, 1991); libraries may be commercially purchased. Libraries with up to $10^9$ to $10^{10}$ unique sequences can be readily generated in such DNA backbones. After generation of the DNA library, the library is cloned into a first primer. The first primer serves as a "cassette", which is inserted into the retroviral construct. The first primer generally contains a number of elements, including for example, the required regulatory sequences (e.g., translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc. See U.S. Ser. No. 08/789,333, hereby incorporated by reference.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in the examples.

The retroviruses may include inducible and constitutive promoters. For example, there are situations wherein it is necessary to induce peptide expression only during certain phases of the selection process. For instance, a scheme to provide pro-inflammatory cytokines in certain instances must include induced expression of the peptides. This is because there is some expectation that over-expressed pro-inflammatory drugs might in the long-term be detrimental to cell growth. Accordingly, constitutive expression is undesirable, and the peptide is only turned on during that phase of the selection process when the phenotype is required, and then shut the peptide down by turning off the retroviral expression to confirm the effect or ensure long-term survival of the producer cells. A large number of both inducible and constitutive promoters are known.

In this manner the primers create a library of fragments, each containing a different random nucleotide sequence that may encode a different peptide. The ligation products are then transformed into bacteria, such as *E. coli*, and DNA is prepared from the resulting library, as is generally outlined in Kitamura, Proc. Natl. Acad. Sci. USA 92:9146-9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+ gag-pol and retrovirus envelope; PA317; and cell lines outlined in Markowitz et al., Virology 167:400 (1988), Markowitz et al., J. Virol. 62:1120 (1988), Li et al., Proc. Natl. Acad. Sci. USA 93:11658 (1996), Kinsella et al., Human Gene Therapy 7:1405 (1996), all of which are incorporated by reference.

In a preferred embodiment, the cell lines disclosed above, and the other methods for producing retrovirus, are useful for production of virus by transient transfection. The virus can either be used directly or be used to infect another retroviral producer cell line for "expansion" of the library.

In certain embodiments, a peptide library is tested for bioactivity using one of the assays described below.

In the event it is not possible to test every member of a library for bioactivity, the library may be deliberately biased. For example, a cyclic peptide can be biased to cellular entry by fixing one or more relatively hydrophobic amino acids, such as tyrosine or tryptophan. Other types of biased libraries which may be synthesized include libraries which primarily contain cyclic peptides comprising amino acids with large side chains and libraries in which the number of cyclic peptide conformers is restricted.

Highly restrained cyclic peptide libraries are made by using codons which code mainly for amino acids with large side chains. That is, when several residues of a cyclic peptide encode amino acids with large side chains, the conformation space of the peptide is restricted. The result is to bias the peptide to a higher affinity by reducing peptide conformational entropy. For example, a library of cyclic peptides could be created by restricting the triplet nucleotides coding for each random amino acid in the library to C or T for the first position of the triplet, A, G or T for the second position in the triplet, and G, C or T for the third position in the triplet. This would result in a library biased to large amino acids, i.e., phenylalanine (F), leucine (L), tyrosine (Y), histidine (H), glutamine (Q), cysteine (C), tryptophan (W) and arginine (R). A library biased toward large amino acid side chains, combined with the loss of glycine, alanine, serine, threonine, aspartate, and glutamate results in a library coding for more rigid peptides. As this library lacks an acidic amino acid, a pre-synthesized triplet coding glutamate (i.e., GAG) or aspartate (GAC) may be added during the DNA synthesis of the library. In particular, since the cyclic compounds of the invention have a low number of residues (e.g., 3 amino acid residues), the compounds are highly conformationally restrained, and, as such, bind target molecules with high affinity and specificity. In other words, the subject compounds are small and highly conformationally restrained, allowing them bind to target molecules with higher affinity and specificity than larger molecules.

Alternatively, a large amino acid side chain residue library may be created by pre-synthesizing triplets for desired residues. These residues are then mixed together during the DNA synthesis of the library. An example of a pre-synthesized large residue library is a library coding tyrosine (Y), arginine (R), glutamic acid (E), histidine (H), leucine (L), glutamine (Q), and optionally proline (P) or threonine (T).

As will be appreciated by those in the art, the type of cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a cyclic peptide. As is more fully described below, cell types implicated in a wide variety of disease conditions are particularly useful, so long as a suitable screen may be designed to allow the selection of cells that exhibit an altered phenotype as a consequence of the presence of a cyclic peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

The skilled artisan will appreciate that, in certain applications of the present invention, non-mammalian cells may be used. In particular, yeast cells may be employed In one embodiment, the cells may be genetically engineered, that is, contain exogenous nucleic acid, for example, to contain target molecules.

Once made, the compositions of the invention find use in a number of applications. In particular, compositions with altered cyclization efficiency are made. The compositions of the invention also may be used to: (1) alter cellular phenotypes and/or physiology; (2) used in screening assays to identify target molecules associated with changes in cellular phenotype or phyisology; (3) used to inhibit protein-protein interactions; (4) used as drugs to treat a number of disease states, such as cancer, cardiovascular diseases, obesity, neurological disorders, etc.; and (5) used as drug leads to develop drugs to treat disease states.

In a preferred embodiment, inteins with altered cyclization activity are generated. Naturally occurring inteins are mutagenized and tested in vivo to determine whether the modified intein can catalyze protein or peptide cyclization in mammalian cells. Preferably, inteins so modified are characterized by more efficient cyclization kinetics in vivo or by the expression level of intein catalyzed cyclization scaffolds. Additional rounds of mutagenesis may be done to optimize in vivo function. Assays useful for measuring intein-catalyzed cyclization efficiency include fluorescent or gel-based assays directly measuring cyclic peptide or protein levels, and functional assays based on the production of a functional cyclic peptide whose effects can be measured or selected for.

In a preferred embodiment, random mutagenesis (e.g., M13 primer mutagenesis and PCR mutagenesis), PCR shuffling or other directed evolution techniques are directed to a target codon or region and the resulting intein variants screened for altered cyclization activity. These techniques are well known and can be directed to predetermined sites, e.g., intein open reading frame or more specific regions or codons within.

In certain embodiments, intein mutants are generated using PCR mutagenesis. The resulting mutants are screened for altered cyclization activity. By "altered" cyclization activity" refers to any characteristic or attribute of an intein that can be selected or detected and compared to the corresponding property of a naturally occurring intein. These properties include cyclization efficiency, stability, etc. Cyclization efficiency may be affected by the presence or absence of a given amino acid, the size of the peptide library, etc. Unless otherwise specified, "altered" cyclization activity, when comparing the cyclization efficiency of a mutant intein to the cyclization efficiency of wild-type or naturally occurring intein is preferably at least 1-fold, more preferably at least a 10-fold increase in activity.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the peptide molecular library, i.e., a different peptide (or nucleic acid encoding the peptide), although as will be appreciated by those in the art, some cells within the library may not contain a peptide, and some may contain more than species of peptide. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, etc.

In a preferred embodiment, the fusion nucleic acids are introduced into a first plurality of cells, and the effect of the peptide is screened in a second or third plurality of cells, different from the first plurality of cells, i.e., generally a different cell type. That is, the effect of the bioactive peptide is due to an extracellular effect on a second cell, i.e., an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

Thus, the methods of the present invention comprise introducing a molecular library of fusion nucleic acids encoding randomized peptides fused to scaffold into a plurality of cells, a cellular library. Each of the nucleic acids comprises a different nucleotide sequence encoding scaffold with a random peptide. The plurality of cells is then screened, as is more fully outlined below, for a cell exhibiting an altered phenotype. The altered phenotype is due to the presence of a bioactive peptide.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e., half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive peptide can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the fusion nucleic acid was introduced; in other embodiments, the altered phenotype is detected in a second cell which is responding to some molecular signal from the first cell.

An altered phenotype of a cell indicates the presence of a bioactive peptide, acting preferably in a transdominant way. By "transdominant" herein is meant that the bioactive peptide indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide is the ability to inhibit NF-KB signaling by binding to IKB-α at a region critical for its function, such that in the presence of sufficient amounts of the peptide (or molecular entity), the signaling pathways that normally lead to the activation of NF-KB through phosphorylation and/or degradation of IKB-α are inhibited from acting at IKB-α because of the binding of the peptide or molecular entity. In another instance, signaling pathways that are normally activated to secrete IgE are inhibited in the presence of peptide. Alternatively, signaling pathways in adipose tissue cells, normally quiescent, are activated to metabolize fat. In yet a further aspect, intracellular mechanisms for the replication of certain viruses, such as HIV-I, or Herpes viridae family members, or Respiratory Syncytia Virus, for example, are inhibited in the presence of a peptide.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent, independent of the β-lactamase, that bound to the β-lactamase in such a way that it enhanced or diminished the function of the β-lactamase by virtue of its binding to β-lactamase.

In a preferred embodiment, once a cell with an altered phenotype is detected, the presence of the fusion protein is verified to ensure that the peptide was expressed and that the altered phenotype is due to presence of the peptide. As will be appreciated by those in the art, this verification of the presence of the peptide can be done either before, during or after the screening for an altered phenotype. This can be done in a variety of ways, although preferred methods utilize FACS techniques.

Once the presence of the fusion protein is verified, the cell with the altered phenotype is generally isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the fusion nucleic acid and/or the bioactive peptide (i.e., the fusion protein) is isolated from the positive cell. This may be done in a number of ways. In a preferred embodiment, primers complementary to DNA regions common to the retroviral constructs, or to specific components of the library such as a rescue sequence, defined above, are used to "rescue" the unique random sequence. Alternatively, the fusion protein is isolated using a rescue sequence. Thus, for example, rescue sequences comprising epitope tags or purification sequences may be used to pull out the fusion protein using immunoprecipitation or affinity columns. In some instances, as is outlined below, this may also pull out the primary target molecule if there is a sufficiently strong binding interaction between the bioactive peptide and the target molecule. Alternatively, the peptide may be detected using mass spectroscopy.

Once rescued, the sequence of the bioactive peptide and/or fusion nucleic acid is determined. This information can then be used in a number of ways.

In a preferred embodiment, the bioactive peptide is resynthesized and reintroduced into the target cells to verify the effect. This may be done using retroviruses, or alternatively using fusions to the HIV-1 Tat protein, and analogs and related proteins, which allows very high uptake into target cells. See for example, Fawell et al., Proc. Natl. Acad. Sci. USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of a bioactive peptide is used to generate more candidate peptides. For example, the sequence of the bioactive peptide may be the basis of a second round of (biased) randomization, to develop bioactive peptides with increased or altered activities. Alternatively, the second round of randomization may change the affinity of the bioactive peptide. Furthermore, it may be desirable to put the identified random region of the bioactive peptide into other presentation structures, or to alter the sequence of the constant region of the presentation structure, to alter the conformation/shape of the bioactive peptide. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive peptide or the bioactive nucleic acid encoding it is used to identify target molecules, i.e., the molecules with which the bioactive peptide interacts. As will be appreciated by those in the art, there may be primary target molecules to which the bioactive peptide binds or acts upon directly, and there may be secondary target molecules, which are part of the signalling pathway affected by the bioactive peptide; these might be termed "validated targets".

In a preferred embodiment, the bioactive peptide is a drug. As will be appreciated by those in the art, the structure of the cyclic peptide may be modeled and used in rational drug design to synthesize agents that mimic the interaction of the cyclic peptide with its' target. Drugs may also be modeled based on the three dimensional structure of the peptide bound to its target. Drugs so modeled may have structures that are similar to or unrelated to the starting structure of the cyclic peptide or the cyclic peptide bound to its target. Alternatively, high throughput screens can be used to identify small molecules capable of competing with the cyclic peptide for its target.

In a preferred embodiment, the bioactive cyclic peptide may be used as the starting point for designing/synthesizing derivative molecules with similar or more favorable properties for use as a drug. For example, individual amino acids, specific chemical groups, etc., can be replaced and the derivative molecule tested for use as a drug. Both naturally occurring and synthetic amino acid analogs (see below for definition) can be introduced in to the derivative molecule to optimize properties such as binding, stability, and pharmocokinectics. Preferably, the derivative molecule has one or more of the following properties: improved stability, higher binding affinity, improved specificity for the target, improved pharmocokinetics, e.g., absorption, distribution, resistance to degradation, etc.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive peptide is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the present methods are useful in cancer applications. The ability to rapidly and specifically kill tumor cells is a cornerstone of cancer chemotherapy. In general, using the methods of the present invention, random libraries can be introduced into any tumor cell (primary or cultured), and peptides identified which by themselves induce apoptosis, cell death, loss of cell division or decreased cell growth. This may be done de novo, or by biased randomization toward known peptide agents, such as angiostatin, which inhibits blood vessel wall growth. Alternatively, the methods of the present invention can be combined with other cancer therapeutics (e.g., drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

In other embodiments, the present compounds may be screened to identify compounds that inhibit metastases, tumor growth, cell proliferation, cell viability, cell damage, and the like.

In a certain embodiments, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate libraries can then be inserted into these cells under the above conditions, and peptides isolated which block or diminish the growth and/or release of the virus. As with chemotherapeutics, these experiments can also be done with drugs which are only partially effective towards this outcome, and bioactive peptides isolated which enhance the virucidal effect of these drugs. Bioactive peptides may also be tested for the ability to block some aspect of viral assembly, viral replication, entry or infectious cycle.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+ mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians. The extracellular anchored constructs offer superb tools for such a discovery. Into the transmembrane, epitope tagged, glycine-serine tethered constructs (ssTM V G20 E TM), one can place a random, cyclized peptide library of the general sequence CNNNNNNNNNNC or C—$(X)_n$—C. Then one infects a cell line that expresses CCR-5 with retroviruses containing this library. Using an antibody to CCR-5 one can use FACS to sort desired cells based on the binding of this antibody to the receptor. All cells which do not bind the antibody will be assumed contain inhibitors of this antibody binding site. These inhibitors, in the retroviral construct can be further assayed for their ability to inhibit HIV-1 entry.

In other embodiments, the present invention finds use with infectious organisms. Intracellular organisms such as mycobacteria, listeria, salmonella, pneumocystis, yersinia, leishmania, *T. cruzi*, can persist and replicate within cells, and become active in immunosuppressed patients. There are currently drugs on the market and in development which are either only partially effective or ineffective against these organisms. Candidate libraries can be inserted into specific cells infected with these organisms (pre- or post-infection), and bioactive peptides selected which promote the intracellular destruction of these organisms in a manner analogous to intracellular "antibiotic peptides" similar to magainins. In addition peptides can be selected which enhance the cidal properties of drugs already under investigation which have insufficient potency by themselves, but when combined with a specific peptide from a candidate library, are dramatically more potent through a synergistic mechanism. Finally, bioactive peptides can be isolated which alter the metabolism of these intracellular organisms, in such a way as to terminate their intracellular life cycle by inhibiting a key organismal event.

In other embodiments, the present methods are useful in immunobiology, inflammation, and allergic response applications. Selective regulation of T lymphocyte responses is a desired goal in order to modulate immune-mediated diseases in a specific manner. Candidate libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

For example, the release of inflammatory mediators (cytokines, leukotrienes, prostaglandins, platelet activating factor, histamine, neuropeptides, and other peptide and lipid mediators) is a key element in maintaining and amplifying aberrant immune responses. Candidate libraries can be inserted into MLs, mast cells, eosinophils, and other cells participating in a specific inflammatory response, and bioactive peptides selected which inhibit the synthesis, release and binding to the cognate receptor of each of these types of mediators.

The present invention also allows the identification of: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a random peptide to a protein binding region to allow interactions with molecules sterically close, i.e., within a signalling pathway, to localize the effects to a functional area of interest.

A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes, but is not limited to, the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below. In a preferred embodiment, the protein is a dominant negative as described herein.

Sequences encoding a ubiquitin conjugating agent may also be used to make variants thereof that are suitable for use in the methods and compositions of the present invention. The ubiquitin conjugating agents and variants suitable for use in the methods and compositions of the present invention may be made as described herein.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the subject invention.

Example 1

Cells producing a library of cyclic 3-mer cyclic peptides were constructed using methods identical to those of Kinsella et al (J Biol. Chem. 2002 277:37512-8), except different oligonucleotides were used for library construction. Clones from this library were screened in an assay to identify IRES-inhibitory compounds.

In summary, three separate 3-mer cyclic peptide libraries were constructed such that the number one position contained a fixed Ser, Thr or Cys residue and the remaining two residues were randomized. These libraries were designated as 1S3, 1T3 and 1C3, respectively. For library construction, degenerate oligonucleotide pools encoding random 3-mer cyclic peptide libraries 5'-AAGATCATATGACATCATCGTCCA-CAAC(AGC/ACC/TGC)(NNK)$_3$TGCATCAGC GGCGA-CAG-3' (SEQ ID NO:1)were annealed to the primer 5'-CT-TGCCGGTGCTGGCCAGGCTGATCAGGCTGTCGCCG-CTGATGCA-3' (SEQ ID NO:2) and extended using the Expand PCR kit (Roche Molecular Biochemicals). The double-stranded DNA insert was digested and inserted into the BclI/DrdI sites of DnaBO-e-BFP (ACUC). The plasmid libraries were electroporated into ElectroMAX DH10B competent *E. coli* (Invitrogen) for amplification on LB+amp agar medium. The total number of primary transformants of these libraries were estimated at $5.6\times10^3$, $5.75\times10^3$, $5.5\times10^3$ for the 1S3, 1T3 and 1C3 libraries, respectively.

Infectious retroviral particles were produced by transfection of 15 μg of each library (as described in Swift et al, (1999) Current Protocols in Immunology Vol. 10.17C, pp. 1-17, Freeman, New York.) into approximately $5\times10^6$ Phoenix-A packaging cells. Each resulting library of retroviral particles was then used to infect $5\times10^6$ BJAB-S3A10 reporter cells and a FACS based selection was carried out to isolate cells with reduced HCV-IRES reporter output.

In detail, the cells used in the assay contained an IRES-dependent reporter system. The IRES dependent reporter system contains a CMV promoter that drives the transcription of an RNA containing an HCV IRES, operably linked to a dual function reporter protein-encoding RNA. Translation of the dual function reporter protein is dependent on the activity of the IRES. Expression of the dual function reporter, HBEGF-2A-GFP, leads to expression of both HBEGF and GFP. Expression of HBEGF sensitizes the cells to be killed by diphtheria toxin whereas GFP expression may be monitored by a fluorescence detector. Also present in the cells is a control reporter system for assaying the activity of 5' cap-dependent translation (the mechanism by which cellular proteins are typically translated). The control reporter system contains a CMV promoter that drives the transcription of an RNA containing 5' cap-dependent UTR, operably linked to an RNA encoding RFP (red fluorescent protein). Translation RFP is dependent on the activity of the 5' cap-dependent UTR.

Cells containing both the cyclic compound library and the reporter systems described above were first screened for survival upon exposure to diptheria toxin, and screened by FACS to identify cells that had reduced GFP expression, as compared to RFP expression. The amino acid sequences of the cyclic compounds set forth below were revealed by sequencing the nucleic acids encoding those peptides.

Cyclic compounds were scored by their IRES-inhibitory activity (based on relative GFP and RFP fluorescence). A score of 1.20 or below indicates that a particular cyclic compound has no significant activity, whereas a score above 1.20 indicates that a particular cyclic compound has significant IRES-inhibitory activity. Cyclic compounds assigned higher scores have a greater IRES-inhibitory activity. The screening assays identified the cyclic compounds of FIG. 2 as having significant IRES-inhibitory activity. The cyclic compounds of FIG. 2 are associated with the following activity scores: II: 1.81 (TMW), III: 3.95 (SAW), IV: 2.37 (SWW), V: 2.16 (TYW), VI: 2.65 (SAV), VII: 1.43 (SVV), VIII: 1.42 (SIV).

It is evident from the above discussion that the subject invention provides an important new class of small, cyclic compounds, as well as an important new means for the production of those compounds. Further, since IRES-mediated translation is required for expression of a wide array of deadly virus, the above-described compounds may be used as effective anti-viral agents for those viruses. Further, since the above-described compounds are cyclic they are conformationally restricted and, as such, exhibit increased specificity and affinity in binding to other molecules, as compared to linear compounds. Further, the above-described cyclic compounds are thought to be more stable in cells and on the shelf than linear compounds, and may be small enough to avoid recognition by host immune system and to cross the plasma membrane of a cell. As such, the subject methods and compositions find use in a variety of different applications, including research, medical, therapeutic and other applications. Accordingly, the present invention represents a significant contribution to the art.

What is claimed is:

1. A cyclic peptide consisting of three genetically encodable amino acid residues, wherein at least one of said amino acid residues is a serine, threonine, or cysteine;

wherein said cyclic peptide is of the formula:

(I)

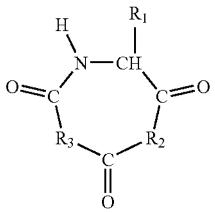

wherein $R_1$ is a side chain of serine, threonine or cysteine; and wherein $R_2$ and $R_3$ are, independently:

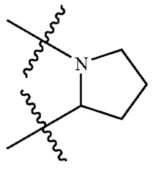

or

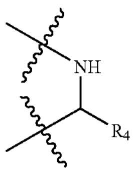

wherein $R_4$ is a side-chain of any genetically encodable amino acid.

2. The cyclic peptide of claim 1, wherein said cyclic peptide has a structure chosen from the following:

(II)

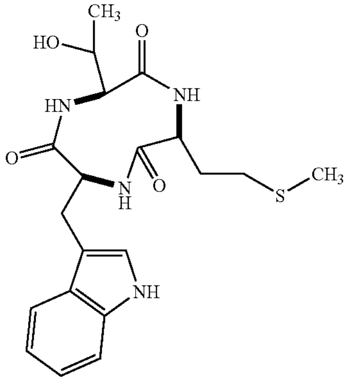

-continued (III)

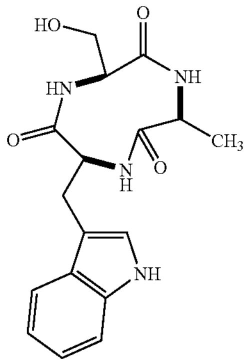

(IV)

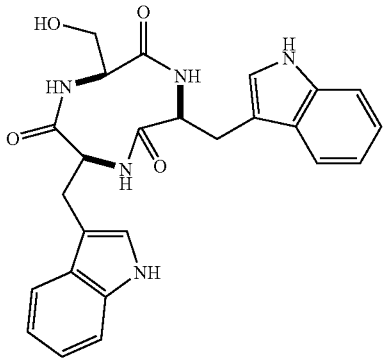

(V)

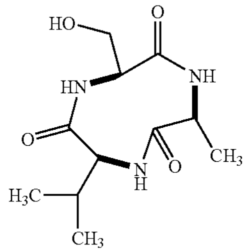

(VI)

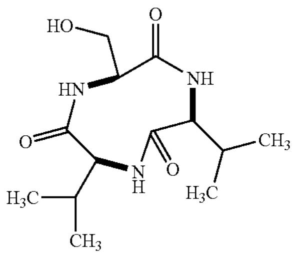

-continued (VII)

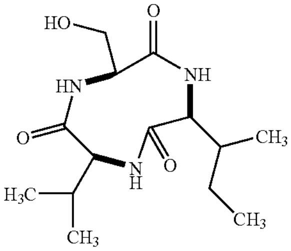

(VIII)

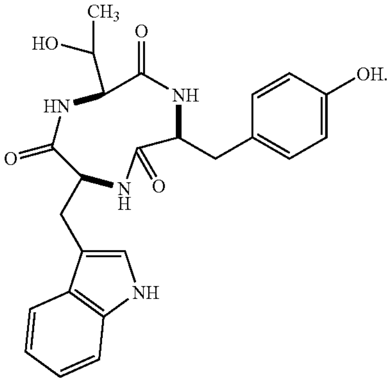

3. A composition comprising:

a pharmaceutically acceptable excipient; and a cyclic peptide-of claim 1.

4. An isolated cyclic peptide consisting of three genetically encodable amino acid residues, wherein at least one of said amino acid residues is a serine, threonine, or cysteine;

wherein said cyclic peptide is of the formula:

(I)

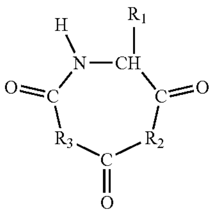

wherein $R_1$ is a side chain of serine, threonine or cysteine; and wherein $R_2$ and $R_3$ are, independently:

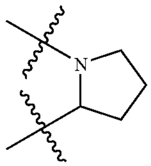

or

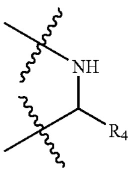

wherein $R_4$ is a side-chain of any genetically encodable amino acid.

* * * * *